US008562999B2

(12) United States Patent
Khandke et al.

(10) Patent No.: US 8,562,999 B2
(45) Date of Patent: *Oct. 22, 2013

(54) FORMULATIONS WHICH STABILIZE AND INHIBIT PRECIPITATION OF IMMUNOGENIC COMPOSITIONS

(71) Applicant: Wyeth LLC, Madison, NJ (US)

(72) Inventors: Lakshmi Khandke, Nanuet, NY (US); Ronald Malone, Chapel Hill, NC (US); Cindy Xudong Yang, Tappan, NY (US); Hanyoung Han, Sunnyside, NY (US); Jee Loon Look, Boyds, MD (US); Zhaowei Jin, Chesterfield, MO (US); Robert C. Seid, Jr., Chapel Hill, NC (US); Ying Chen, Apex, NC (US)

(73) Assignee: Wyeth LLC, Madison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/631,573

(22) Filed: Sep. 28, 2012

(65) Prior Publication Data

US 2013/0034580 A1    Feb. 7, 2013

Related U.S. Application Data

(62) Division of application No. 13/070,664, filed on Mar. 24, 2011, which is a division of application No. 11/737,674, filed on Apr. 19, 2007, now Pat. No. 7,935,787.

(60) Provisional application No. 60/795,261, filed on Apr. 26, 2006.

(51) Int. Cl.
    A61K 39/00     (2006.01)
    A61K 39/385    (2006.01)
    C07K 1/00      (2006.01)

(52) U.S. Cl.
    USPC ............... 424/184.1; 424/193.1; 424/197.11; 530/350

(58) Field of Classification Search
    None
    See application file for complete search history.

(56) References Cited

U.S. PATENT DOCUMENTS

| 4,673,574 | A | 6/1987 | Anderson |
| 4,902,506 | A | 2/1990 | Anderson et al. |
| 4,912,094 | A | 3/1990 | Myers et al. |
| 5,057,540 | A | 10/1991 | Kensil et al. |
| 5,078,996 | A | 1/1992 | Conlon et al. |
| 5,118,794 | A | 6/1992 | Grangeorge et al. |
| 5,163,918 | A | 11/1992 | Righi et al. |
| 5,254,339 | A | 10/1993 | Morein |
| 5,614,382 | A | 3/1997 | Metcalf |
| 5,623,057 | A | 4/1997 | Marburg et al. |
| 5,723,127 | A | 3/1998 | Scott et al. |
| 6,113,918 | A | 9/2000 | Johnson et al. |
| 6,207,646 | B1 | 3/2001 | Krieg et al. |
| 6,224,880 | B1 | 5/2001 | Chan et al. |
| 6,270,775 | B1 | 8/2001 | Cleary |
| 6,355,255 | B1 | 3/2002 | Cleary et al. |
| 6,951,653 | B2 | 10/2005 | Cleary et al. |
| 7,935,787 | B2 | 5/2011 | Khandke et al. |

(Continued)

FOREIGN PATENT DOCUMENTS

| EP | 0941738 A1 | 9/1999 |
| EP | 1296713 B1 | 9/2003 |
| EP | 1326634 B1 | 4/2006 |
| JP | 7236483 A | 9/1995 |
| JP | 10201844 A | 8/1998 |
| RU | 37462 U1 | 4/2004 |
| UA | 67144 A | 6/2004 |
| WO | 8706838 A1 | 11/1987 |
| WO | 90/14837 A1 | 12/1990 |
| WO | 92/19265 A1 | 11/1992 |
| WO | 93/13202 A1 | 7/1993 |
| WO | 94/00153 A1 | 1/1994 |
| WO | 95/17210 A1 | 6/1995 |
| WO | 96/33739 A1 | 10/1996 |
| WO | 97/26008 A1 | 7/1997 |
| WO | 98/13052 A1 | 4/1998 |
| WO | 9851339 A1 | 11/1998 |
| WO | 00/18434 A1 | 4/2000 |

(Continued)

OTHER PUBLICATIONS

Baldwin, R.N., "Contamination of Insulin by Silicone Oil: a Potential Hazard of Plastic Insulin Syringes", Diabetic Medicine, 5:789-790 (1988).
Bartzoka, V., et al., "Protein-Silicone Interactions: How Compatible are the Two Species?", Langmuir, 14 (7):1887-1891 (1998).
Bartzoka, V., et al., "Silicone-Protein Films: Establishing the Strength of the Protein-Silicone Interaction", Langmuir, 14(7):1892-1898 (1998).
Bartzoka, V., et al., "Protein-Silicone Synergism at Liquid/Liquid Interfaces", Langmuir, 16(10):4589-4593 (2000).
Bartzoka, V., et al., "Chapter 21: Protein-Silicone Interactions at Liquid-Liquid Interfaces", Emulsions, Foams and Thin Films, Dekker, New York, Mittel & Kumar (eds.), pp. 371-380 (2000).

(Continued)

Primary Examiner — Albert Navarro
(74) Attorney, Agent, or Firm — Victoria S. Molenda

(57) ABSTRACT

The present invention addresses an ongoing need in the art to improve the stability of immunogenic compositions such as polysaccharide-protein conjugates and protein immunogens. The invention broadly relates to novel formulations which stabilize and inhibit precipitation of immunogenic compositions. More particularly, the invention described hereinafter, addresses a need in the art for formulations which stabilize and inhibit particulate formation (e.g., aggregation, precipitation) of immunogenic compositions which are processed, developed, formulated, manufactured and/or stored in container means such as fermentors, bioreactors, vials, flasks, bags, syringes, rubber stoppers, tubing and the like.

22 Claims, 9 Drawing Sheets

(56) References Cited

U.S. PATENT DOCUMENTS

| | | | |
|---|---|---|---|
| 2004/0047882 A1 | 3/2004 | Broeker | |
| 2006/0134142 A1* | 6/2006 | Kasper et al. | 424/244.1 |
| 2006/0210557 A1 | 9/2006 | Luisi et al. | |
| 2006/0228380 A1* | 10/2006 | Hausdorff et al. | 424/244.1 |
| 2008/0069835 A1 | 3/2008 | Boutriau et al. | |

FOREIGN PATENT DOCUMENTS

| | | | |
|---|---|---|---|
| WO | 00/56360 | A2 | 9/2000 |
| WO | 00/62801 | A2 | 10/2000 |
| WO | 01/41800 | A2 | 6/2001 |
| WO | 02/05846 | A1 | 1/2002 |
| WO | 02/098368 | A2 | 12/2002 |
| WO | 02/098369 | A2 | 12/2002 |
| WO | 03/039485 | A2 | 5/2003 |
| WO | 03/063766 | A2 | 8/2003 |
| WO | 2004/065603 | A2 | 8/2004 |
| WO | 2004/067030 | A2 | 8/2004 |
| WO | 2004/071439 | A2 | 8/2004 |
| WO | 2004/083251 | A2 | 9/2004 |
| WO | 2004/094596 | A2 | 11/2004 |
| WO | 2005/000244 | A2 | 1/2005 |
| WO | 2005/039620 | A1 | 5/2005 |
| WO | 2006/110381 | A1 | 10/2006 |
| WO | 2007/127668 | A2 | 11/2007 |
| WO | 2008/079653 | A1 | 7/2008 |
| WO | 2008/079732 | A2 | 7/2008 |
| WO | 2008/143709 | A2 | 11/2008 |
| WO | 2009/109550 | A1 | 9/2009 |

OTHER PUBLICATIONS

Bernstein, R.K., "Clouding and Deactivation of Clear (Regular) Human Insulin: Association With Silicone Oil From Disposable Syringes?", Diabetes Care, 10(6):786-787 (1987).

Bolgiano, B., et al., "Effect of physico-chemical modification on the immunogenicity of *Haemophilus infiuenzae* type b oligosaccharide-CRM197 conjugate vaccines", Vaccine, 19:3189-3200 (2001).

Chantelau, E.A., et al., "Pollution of Insulin With Silicone Oil, a Hazard of Disposable Plastic Syringes", The Lancet, 1:1459 (1985).

Chantelau, E., et al., "Silicone Oil Released From Disposable Insulin Syringes", Diabetes Care, 9(6):672-673 (1986).

Chantelau, E., "Silicone oil contamination of insulin", Diabetic Medicine, 6:278 (1989).

Chen, C-C, et al., "Immunogenicity and Reactogenicity of Two Recombinant Hepatitis B Vaccines in Healthy Adolescents on Two-dose Schedule", Acta Pediatrica SINICA, 40(3):157-160 (1999).

Collier, F.C., et al., "Insulin Syringes and Silicone Oil", The Lancet, 326:611 (1985).

Dawson, et al.; Handbook of Biochemist, pp. 352-353; 238-239; 357-358 (1991).

Gunn, K.E., et al., "A role for the unfolded protein response in optimizing antibody secretion", Molecular Immunology, 41:919-927 (2004).

Ho, M.M., et al., "Solution stability studies of the subunit components of meningococcal C oligosaccharide-CRM197 conjugate vaccines", Biotechnol. Appl. Biochem., 33:91-98 (2001).

Ho, M.M, et al., "Physico-chemical and immunological examination of the thermal stability of tetanus toxoid conjugate vaccines", Vaccine, 20:3509-3522 (2002).

Jones, L.S., et al., "Silicone Oil Induced Aggregation of Proteins", Journal of Pharmaceutical Sciences, 94(4):918-927 (2005).

Kajihara, M., et al., "Development of new drug delivery system for protein drugs using silicone (I)", Journal of Controlled Release, 66:49-61 (2000).

Khandke, L., et al., "Preservative of choice for Prev(e)nar 13TM in a multi-dose formulation", Vaccine, 29 (41):7144-7153 (2011).

Meyer, B.K., et al. "Antimicrobial Preservative Use in Parenteral Products: Past and Preseny", Journal of Pharmaceutical Sciences, 96(12):3155-3167 (2007).

PCT International Search Report for PCT/US2007/066959 mailed Jul. 28, 2008.

Poulin, J.B., "The Ins and Outs of Prefilled Syringes", Pharmaceutical and Medical Packaging News, available at http://www.pmpnews.com/article/ins-and-outs-prefilled-syringes, 7 pages (2003).

Sun, L., et al., "Protein denaturation induced by cyclic silicone", Biomaterials, 18:1593-1597 (1997).

Yoshida, H., et al., "XBP1 mRNA is Induced by ATF-6 and Spliced by IRE1 in Response to ER Stress to Produce a Highly Active Transcription Factor", Cell, 107(7):881-891 (2001).

Drain, P.K., et al., "Single-dose versus multi-dose vaccine vials for immunization programmes in developing countries", Bull World Health Organ, 81(10)726-731 (2003).

Fernsten, P., et al., "13-valent pneumococcal conjugate vaccine immune sera protects against pneumococcal serotype 1, 3, and 5 bacteremia in a neonatal rat challenge model", Hum Vaccin, 7:Suppl 75-84 (2011).

Paoletti, L.C., "Potency of clinical group B streptococcal conjugate vaccines", Vaccine 19:2118 (2001).

Sharma, B., et al., "A simple and rapid method for quantifying 2-phenoxyethanol (2-PE) in Diphtheria, Tetanus and w-Pertussis (DTwP) vaccine", Biologicals, 36(1).61-63 (2008).

Wilson, G.S., Chapter 7: Faulty Production: Bacterial Contamination of Vaccine or Antiserum:, The Hazards of Immunization, The Athlone Press, London, pp. 75-78 (1967).

Okano, T., "Shin-Yakuzaigaku Souron (New General Pharmaceutical Science)", 3rd edition (Nankoudou Co., Ltd., Tokyo, Japan), pp. 34-36 (1987).

Spoulou, V.I., et al., "Immunogenicity and immunological memory induced by a 7-valent pneumococcal CRM197 conjugate vaccine in symptomatic HIV-1 infected children", Vaccine, 23:5289-5293 (2005).

Wang, W., "Instability, stabilization, and formulation of liquid protein pharmaceuticals"; International Journal of Pharmaceutics, 185:129-188 (1999).

Young, B.R., et al., "Protein Adsorption on Polymeric Biomaterials, I. Adsorption Isotherms", Journal of Colloid and Interface Science, 124(1)-28-43 (1988).

* cited by examiner

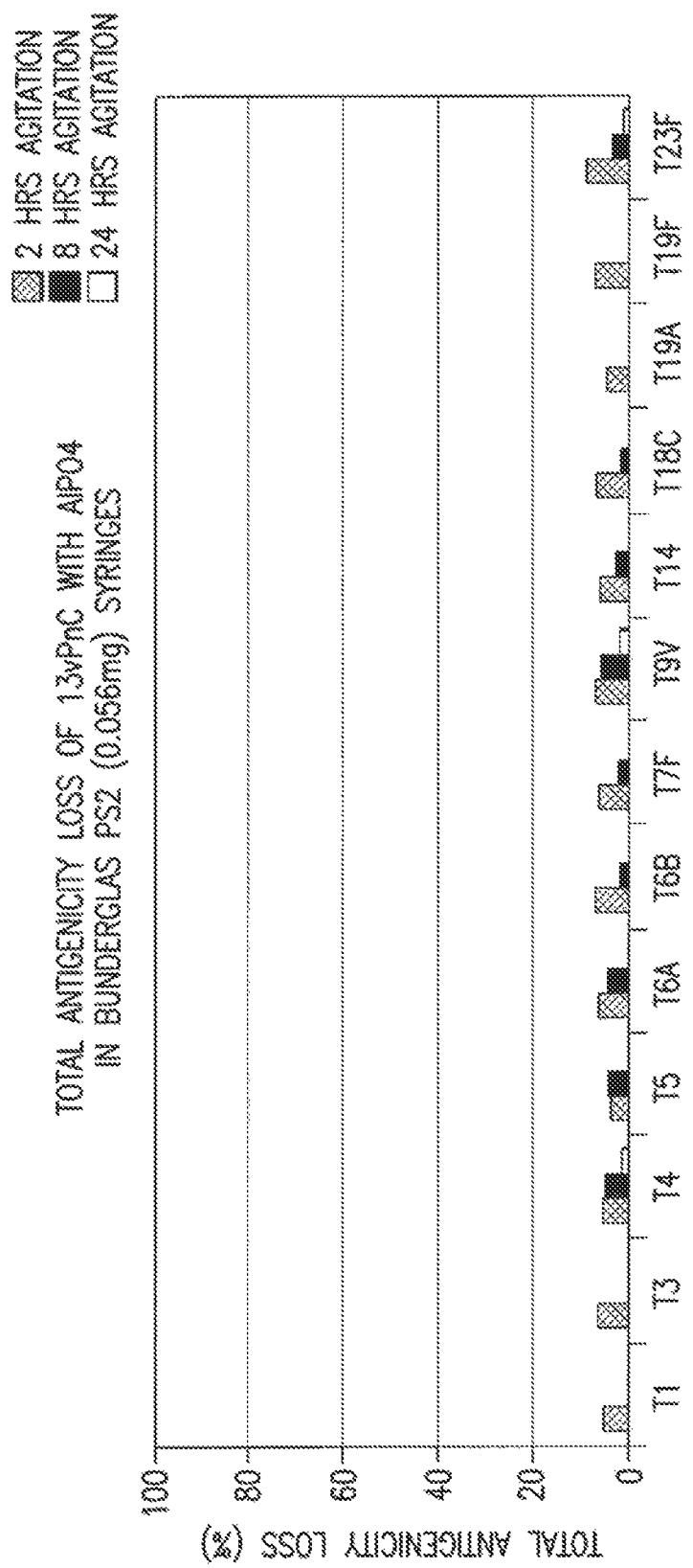

FORMULATIONS WHICH STABILIZE AND INHIBIT PRECIPITATION OF IMMUNOGENIC COMPOSITIONS

CROSS-REFERENCE TO RELATED APPLICATIONS

This application is a divisional application of U.S. application Ser. No. 13/070,664, filed Mar. 24, 2011, which is a divisional application of U.S. application Ser. No. 11/737,674, filed Apr. 19, 2007, which claims the benefit of U.S. Provisional Application No. 60/795,261, filed Apr. 26, 2006. The contents of application Ser. Nos. 13/070,664; 11/737,674 and 60/795,261 are hereby incorporated by reference in their entirety.

FIELD OF THE INVENTION

The present invention generally relates to the fields of immunology, bacteriology, vaccine formulation, protein stability and process development. More particularly, the invention relates to novel formulations which inhibit precipitation of immunogenic compositions.

BACKGROUND OF THE INVENTION

It is generally accepted in the bio-pharmaceutical arts, that improving the stability of an immunogenic composition (e.g., a protein immunogen, a polysaccharide-protein conjugate) is a necessary and highly desirable goal. For example, an immunogenic composition must appear fresh, elegant and professional when administered to a patient. Any changes in stability and/or physical appearance of the immunogenic composition, such as color change, clouding or haziness, may cause a patient or consumer to lose confidence in the product. Furthermore, because many immunogenic formulations are dispensed in multiple-dose containers, uniformity of dose content of the active ingredient (e.g., a polysaccharide-protein conjugate) over time must be assured (e.g., a cloudy solution can lead to a non-uniform dosage pattern). Additionally, the immunogenic composition must be active throughout its "expected" shelf life, wherein any breakdown of the immunogenic composition to an inactive or otherwise undesired form (e.g., an aggregate) lowers the total concentration of the product.

Several reports in the literature have suggested that the stability of a particular immunogenic composition (e.g., a protein immunogen, a polysaccharide-protein conjugate) is at least in part dependent upon the specific protein or carrier protein (Ho et al., 2001; Ho et al., 2002; Bolgiano et al., 2001). For example, stability analysis of meningococcal C (MenC) polysaccharides and *Haemophilus influenzae* type b (Hib) polysaccharides, conjugated to either a tetanus toxoid (TT) or a $CRM_{197}$ carrier protein, revealed different stability profiles dependent on the carrier protein (Ho et al., 2002). In another study (Ho et al., 2001), MenC-$CRM_{197}$ conjugates from two different manufacturers were analyzed (Ho et al., 2001), wherein the MenC-$CRM_{197}$ conjugates differed in their conjugation chemistry and length of conjugate polysaccharide (both having the same carrier protein, $CRM_{197}$). Data from this study further indicated that factors such as conjugation chemistry (e.g., reductive amination either directly or via a chemical spacer group), number of conjugation sites, polysaccharide chain length, pH, storage buffer, storage temperature(s) and freeze/thaw cycles also influence the stability of an immunogenic composition.

Thus, when developing a formulation for an immunogenic composition, many factors must be considered to ensure a safe, stable, robust and cost effective product. Such considerations include, but are not limited to, chemical stability of the immunogenic composition (e.g., hydrolysis of saccharides, de-polymerization of polysaccharides, proteolysis or fragmentation of proteins), physical/thermal stability of the immunogenic composition (e.g., aggregation, precipitation, adsorption), compatibility of the immunogenic composition with the container/closure system, interactions between immunogenic composition and inactive ingredients (e.g., buffers, salts, excipients, cryoprotectants), the manufacturing process, the dosage form (e.g., lyophilized, liquid), the environmental conditions encountered during shipping, storage and handling (e.g., temperature, humidity, shear forces), and the length of time between manufacture and usage.

It has been suggested in the art, that silicone oil, which induces protein secondary and tertiary conformational changes, might be responsible for the aggregation/precipitation seen in certain protein pharmaceutical preparations (Jones et al., 2005). For example, several reports in the 1980s implicated the release of silicone oil from disposable plastic syringes as the causative agent in the aggregation of human insulin (Chantelau and Berger, 1985; Chantelau et al., 1986; Chantelau, 1989; Bernstein, 1987; Baldwin, 1988; Collier and Dawson, 1985). Chantelau et al. (1986) observed that after three or more withdrawals from a ten-dose preparation of insulin (using a siliconized disposable syringe), the vial would begin clouding due silicone oil contamination, thereby resulting in aggregation and deactivation of the insulin (Chantelau et al., 1986). Paradoxically, silicone oil is a necessary component of plastic syringes, as it serves to lubricate the rubber plunger and facilitate transfer of the plunger down the syringe barrel (i.e., silicone oil improves the syringeability of the formulation).

Furthermore, the use of silicone oil is not limited to syringes, as it is used as a coating for glass vials to minimize protein adsorption, as a lubricant to prevent conglomeration of rubber stoppers during filing procedures, as a lubricant critical to the processability/machinability of glass and elastomeric closures and as a lubricant to ease needle penetration of vial rubber stoppers. Additionally, the siliconization of syringes, glass vials, rubber stoppers and the like, is not a well controlled nor standardized process, and as such, there is a high degree of variability of the silicone oil content from one lot to another.

There is therefore an ongoing need in the art for formulations which enhance stability and inhibit precipitation of immunogenic compositions.

SUMMARY OF THE INVENTION

The present invention broadly relates to novel formulations which stabilize and inhibit precipitation of immunogenic compositions. More specifically in certain embodiments, the present invention is directed to novel formulations which inhibit precipitation of immunogenic compositions comprised in container means. In one specific embodiment, the invention is directed to novel formulations which stabilize immunogenic compositions against silicone oil interactions, shear forces, shipping agitation, and the like.

Thus, in certain embodiments, the invention is directed to formulations which stabilize a polysaccharide-protein conjugate, the formulation comprising (i) a pH buffered saline solution, wherein the buffer has a pKa of about 3.5 to about 7.5, (ii) a surfactant and (iii) one or more polysaccharide-protein conjugates. In one specific embodiment, the polysaccharide-protein conjugate formulation is comprised in a container means. In certain embodiments, the container means is selected from one or more of the group consisting of a vial, a vial stopper, a vial closure, a glass closure, a rubber closure, a plastic closure, a syringe, a syringe stopper, a syringe plunger, a flask, a beaker, a graduated cylinder, a fermentor, a bioreactor, tubing, a pipe, a bag, a jar, an ampoule, a cartridge and a disposable pen. In certain embodiments, the container means is siliconized.

In certain embodiments, the pH buffered saline solution of the formulations has a pH of 5.5 to 7.5. In other embodiments, the buffer is phosphate, succinate, histidine or citrate. In certain embodiments, the buffer is succinate at a final concentration of 1 mM to 10 mM and pH 5.8 to 6.0. In one particular embodiment, the final concentration of the succinate buffer is 5 mM. In other embodiments, the salt in the pH buffered saline solution comprises magnesium chloride, potassium chloride, sodium chloride or a combination thereof. In one particular embodiment, the salt in the pH buffered saline solution is sodium chloride.

In another embodiment, the surfactant of the formulations is selected from the group consisting of polysorbate 20 (Tween™20), polysorbate 40 (Tween™40), polysorbate 60 (Tween™60), polysorbate 65 (Tween™65), polysorbate 80 (Tween™80), polysorbate 85 (Tween™85), Triton™ N-101, Triton™ X-100, oxtoxynol 40, nonoxynol-9, triethanolamine, triethanolamine polypeptide oleate, polyoxyethylene-660 hydroxystearate (PEG-15, Solutol H15), polyoxyethylene-35-ricinoleate (Cremophor EL™), soy lecithin and a poloxamer. In one particular embodiment, the surfactant is polysorbate 80. In another embodiment, the final concentration of the polysorbate 80 in formulation is at least 0.01% to 10% polysorbate 80 weight/volume of the formulation. In other embodiments, the final concentration of the polysorbate 80 in the formulation is 0.01% polysorbate 80 weight/volume of the formulation. In yet other embodiments, the final concentration of the polysorbate 80 in the formulation is 0.05% polysorbate 80 weight/volume of the formulation. In another embodiment, the final concentration of the polysorbate 80 in the formulation is 0.1% polysorbate 80 weight/volume of the formulation. In certain other embodiments, the final concentration of the polysorbate 80 in the formulation is 1.0% polysorbate 80 weight/volume of the formulation. In yet other embodiments, the final concentration of the polysorbate 80 in the formulation is 10.0% polysorbate 80 weight/volume of the formulation.

In another embodiment, the polysaccharide-protein conjugate comprises one or more pneumococcal polysaccharides. In certain embodiments, the one or more pneumococcal polysaccharides are a *S. pneumoniae* serotype 4 polysaccharide, a *S. pneumoniae* serotype 6B polysaccharide, a *S. pneumoniae* serotype 9V polysaccharide, a *S. pneumoniae* serotype 14 polysaccharide, a *S. pneumoniae* serotype 18C polysaccharide, a *S. pneumoniae* serotype 19F polysaccharide, a *S. pneumoniae* serotype 23F polysaccharide, a *S. pneumoniae* serotype 1 polysaccharide, a *S. pneumoniae* serotype 3 polysaccharide, a *S. pneumoniae* serotype 5 polysaccharide, a *S. pneumoniae* serotype 6A polysaccharide, a *S. pneumoniae* serotype 7F polysaccharide and a *S. pneumoniae* serotype 19A polysaccharide. In certain embodiments, the protein of the polysaccharide-protein conjugate formulation is selected from the group consisting of $CRM_{197}$, a tetanus toxoid, a cholera toxoid, a pertussis toxoid, an *E. coli* heat labile toxoid (LT), a pneumolysin toxoid, pneumococcal surface protein A (PspA), pneumococcal adhesin protein A (PsaA), a C5a peptidase from *Streptococcus, Haemophilus influenzae* protein D, ovalbumin, keyhole limpet haemocyanin (KLH), bovine serum albumin (BSA) and purified protein derivative of tuberculin (PPD).

In one specific embodiment, the polysaccharide-protein conjugate formulation is a 7-valent pneumococcal conjugate (7vPnC) formulation comprising a *S. pneumoniae* serotype 4 polysaccharide conjugated to a $CRM_{197}$ polypeptide, a *S. pneumoniae* serotype 6B polysaccharide conjugated to a $CRM_{197}$ polypeptide, a *S. pneumoniae* serotype 9V polysaccharide conjugated to a $CRM_{197}$ polypeptide, a *S. pneumoniae* serotype 14 polysaccharide conjugated to a $CRM_{197}$ polypeptide, a *S. pneumoniae* serotype 18C polysaccharide conjugated to a $CRM_{197}$ polypeptide, a *S. pneumoniae* serotype 19F polysaccharide conjugated to a $CRM_{197}$ polypeptide and a *S. pneumoniae* serotype 23F polysaccharide conjugated to a $CRM_{197}$ polypeptide.

In another specific embodiment, the polysaccharide-protein conjugate formulation is a 13-valent pneumococcal conjugate (13vPnC) formulation comprising a *S. pneumoniae* serotype 4 polysaccharide conjugated to a $CRM_{197}$ polypeptide, a *S. pneumoniae* serotype 6B polysaccharide conjugated to a $CRM_{197}$ polypeptide, a *S. pneumoniae* serotype 9V polysaccharide conjugated to a $CRM_{197}$ polypeptide, a *S. pneumoniae* serotype 14 polysaccharide conjugated to a $CRM_{197}$ polypeptide, a *S. pneumoniae* serotype 18C polysaccharide conjugated to a $CRM_{197}$ polypeptide, a *S. pneumoniae* serotype 19F polysaccharide conjugated to a $CRM_{197}$ polypeptide, a *S. pneumoniae* serotype 23F polysaccharide conjugated to a $CRM_{197}$ polypeptide, a *S. pneumoniae* serotype 1 polysaccharide conjugated to a $CRM_{197}$ polypeptide, a *S. pneumoniae* serotype 3 polysaccharide conjugated to a $CRM_{197}$ polypeptide, a *S. pneumoniae* serotype 5 polysaccharide conjugated to a $CRM_{197}$ polypeptide, a *S. pneumoniae* serotype 6A polysaccharide conjugated to a $CRM_{197}$ polypeptide, a *S. pneumoniae* serotype 7F polysaccharide conjugated to a $CRM_{197}$ polypeptide and a *S. pneumoniae* serotype 19A polysaccharide conjugated to a $CRM_{197}$ polypeptide.

In other embodiments, the formulation further comprises one or more meningococcal polysaccharides, one or more meningococcal antigenic proteins, or a combination thereof. In yet other embodiments, the formulation further comprises one or more streptococcal polysaccharides, one or more streptococcal antigenic proteins, or a combination thereof.

In certain other embodiments, the formulation further comprises one or more adjuvants. Exemplary suitable adjuvants are described herein below.

In other embodiments, the invention is directed to formulations which stabilize a streptococcal C5a peptidase (SCP) composition, the formulation comprising (i) a pH buffered saline solution, wherein the buffer has a pKa of about 3.5 to about 6.5, (ii) a surfactant and (iii) a streptococcal C5a peptidase. In one specific embodiment, SCP formulation is comprised in a container means. In certain embodiments, the container means is selected from one or more of the group consisting of a vial, a vial stopper, a vial closure, a glass closure, a rubber closure, a plastic closure, a syringe, a syringe stopper, a syringe plunger, a flask, a beaker, a graduated cylinder, a fermentor, a bioreactor, tubing, a pipe, a bag, a jar, an ampoule, a cartridge and a disposable pen.

In other embodiments, the pH buffered saline solution of the formulation has a pH of 5.5 to 7.5. In other embodiments, the buffer is succinate, histidine, phosphate or citrate. In one specific embodiment, the buffer is succinate at a final concentration of 1 mM to 10 mM and pH 5.8 to 6.0. In another specific embodiment, the final concentration of the succinate buffer is 5 mM. In yet other embodiments, the salt in the pH buffered saline solution comprises magnesium chloride, potassium chloride, sodium chloride or a combination thereof.

In certain embodiments, the surfactant in the formulations is selected from the group consisting of polysorbate 20 (Tween™20), polysorbate 40 (Tween™40), polysorbate 60 (Tween™60), polysorbate 65 (Tween™65), polysorbate 80 (Tween™80), polysorbate 85 (Tween™85), Triton™ N-101, Triton™ X-100, oxtoxynol 40, nonoxynol-9, triethanolamine, triethanolamine polypeptide oleate, polyoxyethylene-660 hydroxystearate (PEG-15, Solutol H15), polyoxyethylene-35-ricinoleate (Cremophor EL™), soy lecithin and a poloxamer. In one specific embodiment, the surfactant is polysorbate 80. In certain embodiments, the final concentration of the polysorbate 80 in formulation is 0.01% to 10% polysorbate 80 weight/volume of the formulation. In yet other embodiments, the final concentration of the polysorbate 80 in the formulation is 0.01% polysorbate 80 weight/volume of the formulation. In other embodiments, the final concentration of the polysorbate 80 in the formulation is 0.05% polysorbate 80 weight/volume of the formulation. In yet other embodiments, the final concentration of the polysorbate 80 in the formulation is 0.1% polysorbate 80 weight/volume of the formulation. In another embodiment, the final concentration of the polysorbate 80 in the formulation is 1.0% polysorbate 80 weight/volume of the formulation. In yet another embodiment, the final concentration of the polysorbate 80 in the formulation is 10.0% polysorbate 80 weight/volume of the formulation.

In certain other embodiments, the SCP composition further comprises one or more polypeptides selected from the group consisting of a streptococcal polypeptide, a pneumococcal polypeptide, a meningococcal polypeptide and a staphylococcal polypeptide. In still other embodiments, the SCP composition further comprises one or more polysaccharides selected from the group consisting of a streptococcal polysaccharide, a pneumococcal polysaccharide, a meningococcal polysaccharide and a staphylococcal polysaccharide.

In another embodiment, the formulation further comprises one or more adjuvants. Exemplary suitable adjuvants are described herein below.

In another embodiment, the invention is directed to formulations which inhibit silicone induced precipitation of a polysaccharide-protein conjugate comprised in a siliconized container means, the formulation comprising (i) a pH buffered saline solution, wherein the buffer has a pKa of about 3.5 to about 7.5, (ii) an aluminum salt and (iii) one or more polysaccharide-protein conjugates. In certain embodiments, the siliconized container means is selected from one or more of the group consisting of a vial, a vial stopper, a vial closure, a glass closure, a rubber closure, a plastic closure, a syringe, a syringe stopper, a syringe plunger, a flask, a beaker, a graduated cylinder, a fermentor, a bioreactor, tubing, a pipe, a bag, a jar, an ampoule, a cartridge and a disposable pen.

In certain embodiments, the pH buffered saline solution in the formulations has a pH of 5.5 to 7.5. In other embodiments, the buffer in the formulations is phosphate, succinate, histidine or citrate. In yet other embodiments, the buffer is succinate at a final concentration of 1 mM to 10 mM and pH 5.8 to 6.0. In one particular embodiment, the final concentration of the succinate buffer is 5 mM. In still other embodiments, the salt in the pH buffered saline solution comprises magnesium chloride, potassium chloride, sodium chloride or a combination thereof. In one particular embodiment, the salt in the pH buffered saline solution is sodium chloride.

In other embodiments, the aluminum salt is aluminum hydroxide, aluminum phosphate or aluminum sulfate. In one specific embodiment, the aluminum salt is aluminum phosphate.

In certain other embodiments, the formulation further comprises polysorbate 80 (Tween™80). In one specific embodiment, the final concentration of the polysorbate 80 in formulation is at least 0.01% to 10% polysorbate 80 weight/volume of the formulation.

In another embodiment, the polysaccharide-protein conjugate comprises one or more pneumococcal polysaccharides. In certain embodiments, the one or more pneumococcal polysaccharides are a S. pneumoniae serotype 4 polysaccharide, a S. pneumoniae serotype 6B polysaccharide, a S. pneumoniae serotype 9V polysaccharide, a S. pneumoniae serotype 14 polysaccharide, a S. pneumoniae serotype 18C polysaccharide, a S. pneumoniae serotype 19F polysaccharide, a S. pneumoniae serotype 23F polysaccharide, a S. pneumoniae serotype 1 polysaccharide, a S. pneumoniae serotype 3 polysaccharide, a S. pneumoniae serotype 5 polysaccharide, a S. pneumoniae serotype 6A polysaccharide, a S. pneumoniae serotype 7F polysaccharide and a S. pneumoniae serotype 19A polysaccharide.

In certain other embodiments, the protein of the polysaccharide-protein conjugate formulation is selected from the group consisting of $CRM_{197}$, a tetanus toxoid, a cholera toxoid, a pertussis toxoid, an *E. coli* heat labile toxoid (LT), a pneumolysin toxoid, pneumococcal surface protein A (PspA), pneumococcal adhesin protein A (PsaA), a C5a peptidase from *Streptococcus, Haemophilus influenzae* protein D, ovalbumin, keyhole limpet haemocyanin (KLH), bovine serum albumin (BSA) and purified protein derivative of tuberculin (PPD).

In one particular embodiment, the polysaccharide-protein conjugate formulation is a 7-valent pneumococcal conjugate (7vPnC) formulation comprising a S. pneumoniae serotype 4 polysaccharide conjugated to a $CRM_{197}$ polypeptide, a S. pneumoniae serotype 6B polysaccharide conjugated to a $CRM_{197}$ polypeptide, a S. pneumoniae serotype 9V polysaccharide conjugated to a $CRM_{197}$ polypeptide, a S. pneumoniae serotype 14 polysaccharide conjugated to a $CRM_{197}$ polypeptide, a S. pneumoniae serotype 18C polysaccharide conjugated to a $CRM_{197}$ polypeptide, a S. pneumoniae serotype 19F polysaccharide conjugated to a $CRM_{197}$ polypeptide and a S. pneumoniae serotype 23F polysaccharide conjugated to a $CRM_{197}$ polypeptide.

In another specific embodiment, the polysaccharide-protein conjugate formulation is a 13-valent pneumococcal conjugate (13vPnC) formulation comprising a S. pneumoniae serotype 4 polysaccharide conjugated to a $CRM_{197}$ polypeptide, a S. pneumoniae serotype 6B polysaccharide conjugated to a $CRM_{197}$ polypeptide, a S. pneumoniae serotype 9V polysaccharide conjugated to a $CRM_{197}$ polypeptide, a S. pneumoniae serotype 14 polysaccharide conjugated to a $CRM_{197}$ polypeptide, a S. pneumoniae serotype 18C polysaccharide conjugated to a $CRM_{197}$ polypeptide, a S. pneumoniae serotype 19F polysaccharide conjugated to a $CRM_{197}$ polypeptide, a S. pneumoniae serotype 23F polysaccharide conjugated to a $CRM_{197}$ polypeptide, a S. pneumoniae serotype 1 polysaccharide conjugated to a $CRM_{197}$ polypeptide, a S. pneumoniae serotype 3 polysaccharide conjugated to a $CRM_{197}$ polypeptide, a S. pneumoniae serotype 5 polysaccharide conjugated to a $CRM_{197}$ polypeptide, a S. pneumoniae serotype 6A polysaccharide conjugated to a $CRM_{197}$ polypeptide, a S. pneumoniae serotype 7F polysaccharide conjugated to a $CRM_{197}$ polypeptide and a *S. pneumoniae* serotype 19A polysaccharide conjugated to a $CRM_{197}$ polypeptide.

In yet other embodiments, the formulation further comprises one or more meningococcal polysaccharides, one or more meningococcal antigenic proteins, or a combination thereof.

In another embodiment, the formulation further comprises one or more streptococcal polysaccharides, one or more streptococcal antigenic proteins, or a combination thereof.

In certain other embodiments, the formulation further comprises one or more adjuvants. Exemplary suitable adjuvants are described herein below.

In other embodiments, the present invention is directed to formulations which inhibit silicone induced precipitation of a streptococcal C5a peptidase (SCP) composition comprised in a siliconized container means, the formulation comprising (i) a pH buffered saline solution, wherein the buffer has a pKa of about 3.5 to about 6.5, (ii) an aluminum salt and (iii) a streptococcal C5a peptidase. In certain embodiments, the container means is selected from one or more of the group consisting of a vial, a vial stopper, a vial closure, a glass closure, a rubber closure, a plastic closure, a syringe, a syringe stopper, a syringe plunger, a flask, a beaker, a graduated cylinder, a fermentor, a bioreactor, tubing, a pipe, a bag, a jar, an ampoule, a cartridge and a disposable pen.

In another embodiment, the pH buffered saline solution of the formulation has a pH of 5.5 to 7.5. In other embodiments, the buffer is succinate, histidine, phosphate or citrate. In certain embodiments, the buffer is succinate at a final concentration of 1 mM to 10 mM and pH 5.8 to 6.0. In another embodiment, the salt in the pH buffered saline solution comprises magnesium chloride, potassium chloride, sodium chloride or a combination thereof.

In certain other embodiments, the formulation further comprises polysorbate 80 (Tween™80). In one specific embodiment, the final concentration of the polysorbate 80 in the formulation is 0.01% to 10% polysorbate 80 weight/volume of the formulation.

In yet other embodiments, the SCP composition further comprises one or more polypeptides selected from the group consisting of a streptococcal polypeptide, a pneumococcal polypeptide, a meningococcal polypeptide and a staphylococcal polypeptide.

In certain other embodiments, the SCP composition further comprises one or more polysaccharides selected from the group consisting of a streptococcal polysaccharide, a pneumococcal polysaccharide, a meningococcal polysaccharide and a staphylococcal polysaccharide.

In yet another embodiment, the formulation further comprises one or more adjuvants. Exemplary suitable adjuvants are described herein below.

In other embodiments, the invention is directed to formulations which stabilize a *N. meningitidis* 2086 protein composition, the formulation comprising (i) a pH buffered saline solution, wherein the buffer has a pKa of about 3.5 to about 6.5, (ii) a surfactant and (iii) a *N. meningitidis* 2086 protein. Exemplary *N. meningitidis* 2086 proteins are described herein below. In one specific embodiment, the *N. meningitidis* 2086 protein formulation is comprised in a container means. In certain embodiments, the container means is selected from one or more of the group consisting of a vial, a vial stopper, a vial closure, a glass closure, a rubber closure, a plastic closure, a syringe, a syringe stopper, a syringe plunger, a flask, a beaker, a graduated cylinder, a fermentor, a bioreactor, tubing, a pipe, a bag, a jar, an ampoule, a cartridge and a disposable pen.

In other embodiments, the pH buffered saline solution of the formulation has a pH of 5.5 to 7.5. In other embodiments, the buffer is succinate, histidine, phosphate or citrate. In one specific embodiment, the buffer is succinate at a final concentration of 1 mM to 10 mM and pH 5.8 to 6.0. In another specific embodiment, the final concentration of the succinate buffer is 5 mM. In yet other embodiments, the salt in the pH buffered saline solution comprises magnesium chloride, potassium chloride, sodium chloride or a combination thereof.

In certain embodiments, the surfactant in the formulations is selected from the group consisting of polysorbate 20 (Tween™20), polysorbate 40 (Tween™40), polysorbate 60 (Tween™60), polysorbate 65 (Tween™65), polysorbate 80 (Tween™80), polysorbate 85 (Tween™85), Triton™ N-101, Triton™ X-100, oxtoxynol 40, nonoxynol-9, triethanolamine, triethanolamine polypeptide oleate, polyoxyethylene-660 hydroxystearate (PEG-15, Solutol H15), polyoxyethylene-35-ricinoleate (Cremophor EL™), soy lecithin and a poloxamer. In one specific embodiment, the surfactant is polysorbate 80. In certain embodiments, the final concentration of the polysorbate 80 in the formulation is 0.01% to 10% polysorbate 80 weight/volume of the formulation. In yet other embodiments, the final concentration of the polysorbate 80 in the formulation is 0.01% polysorbate 80 weight/volume of the formulation. In other embodiments, the final concentration of the polysorbate 80 in the formulation is 0.05% polysorbate 80 weight/volume of the formulation. In yet other embodiments, the final concentration of the polysorbate 80 in the formulation is 0.1% polysorbate 80 weight/volume of the formulation. In another embodiment, the final concentration of the polysorbate 80 in the formulation is 1.0% polysorbate 80 weight/volume of the formulation. In yet another embodiment, the final concentration of the polysorbate 80 in the formulation is 10.0% polysorbate 80 weight/volume of the formulation.

In certain other embodiments, the *N. meningitidis* 2086 protein composition further comprises one or more polypeptides selected from the group consisting of a streptococcal polypeptide, a pneumococcal polypeptide, a meningococcal polypeptide and a staphylococcal polypeptide. In still other embodiments, the *N. meningitidis* 2086 protein composition further comprises one or more polysaccharides selected from the group consisting of a streptococcal polysaccharide, a pneumococcal polysaccharide, a meningococcal polysaccharide and a staphylococcal polysaccharide.

In another embodiment, the formulation further comprises one or more adjuvants. Exemplary suitable adjuvants are described herein below.

In other embodiments, the present invention is directed to formulations which inhibit silicone induced precipitation of a *N. meningitidis* 2086 protein composition comprised in a siliconized container means, the formulation comprising (i) a pH buffered saline solution, wherein the buffer has a pKa of about 3.5 to about 6.5, (ii) an aluminum salt and (iii) a *N. meningitidis* 2086 protein. In certain embodiments, the container means is selected from one or more of the group consisting of a vial, a vial stopper, a vial closure, a glass closure, a rubber closure, a plastic closure, a syringe, a syringe stopper, a syringe plunger, a flask, a beaker, a graduated cylinder, a fermentor, a bioreactor, tubing, a pipe, a bag, a jar, an ampoule, a cartridge and a disposable pen.

In another embodiment, the pH buffered saline solution of the formulation has a pH of 5.5 to 7.5. In other embodiments, the buffer is succinate, histidine, phosphate or citrate. In certain embodiments, the buffer is succinate at a final concentration of 1 mM to 10 mM and pH 5.8 to 6.0. In another embodiment, the salt in the pH buffered saline solution comprises magnesium chloride, potassium chloride, sodium chloride or a combination thereof.

In certain other embodiments, the formulation further comprises polysorbate 80 (Tween™80). In one specific embodiment, the final concentration of the polysorbate 80 in the formulation is 0.01% to 10% polysorbate 80 weight/volume of the formulation.

In yet other embodiments, the *N. meningitidis* 2086 protein composition further comprises one or more polypeptides selected from the group consisting of a streptococcal polypeptide, a pneumococcal polypeptide, a meningococcal polypeptide and a staphylococcal polypeptide.

In certain other embodiments, the *N. meningitidis* 2086 protein composition further comprises one or more polysaccharides selected from the group consisting of a streptococcal polysaccharide, a pneumococcal polysaccharide, a meningococcal polysaccharide and a staphylococcal polysaccharide.

In yet another embodiment, the formulation further comprises one or more adjuvants. Exemplary suitable adjuvants are described herein below.

Other features and advantages of the invention will be apparent from the following detailed description, from the embodiments thereof, and from the claims.

DETAILED DESCRIPTION OF THE INVENTION

Figure 1A:
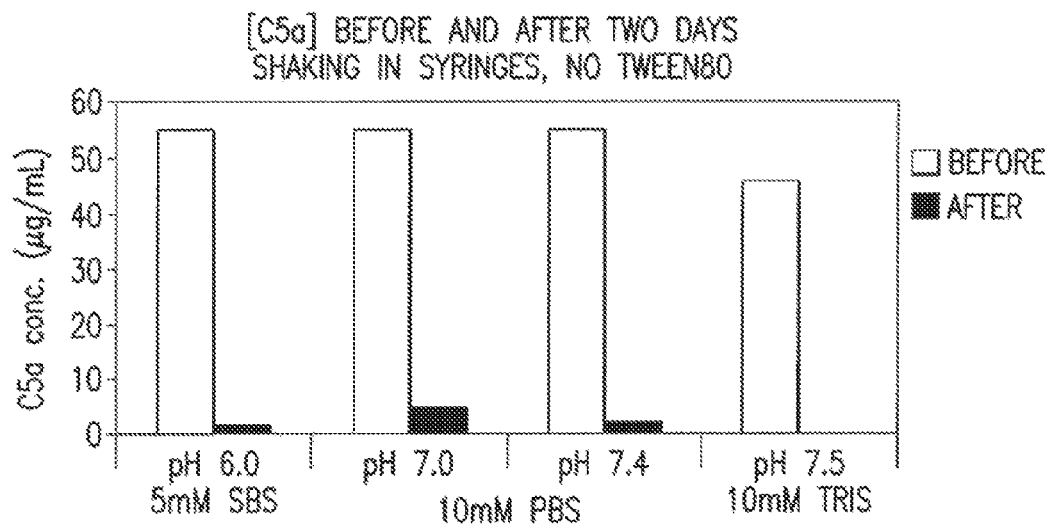
FIG. 1 shows the stability of Streptococcal C5a peptidase (SCP) formulations (filled in syringes) before and after two days of gentle agitation (60 cpm) on a horizontal orbital shaker. The data presented in FIG. 1A is the two day stability of the SCP formulated without any Tween™80 (i.e., 0%), whereas the data in FIG. 1B is the two day stability of the SCP formulated with 0.025% Tween™80. The buffers used in the formulations shown in FIGS. 1A and 1B are succinate buffered saline (SBS), phosphate buffered saline (PBS) and tris (hydroxymethyl)aminomethane (TRIS).

The present invention addresses an ongoing need in the art to improve the stability of immunogenic compositions such as polysaccharide-protein conjugates and protein immunogens. Thus, the present invention broadly relates to novel surfactant formulations and/or novel aluminum salt formulations which stabilize and inhibit precipitation of immunogenic compositions. More particularly, the invention described hereinafter, addresses a need in the art for formulations which stabilize and inhibit particulate formation (e.g., aggregation, precipitation) of immunogenic compositions which are processed, developed, formulated, manufactured and/or stored in container means such as fermentors, bioreactors, vials, flasks, bags, syringes, rubber stoppers, tubing and the like.

As set forth above in the Background of the Invention, various factors influence the stability of immunogenic compositions, including, but not limited to, chemical stability of the immunogenic composition, physical/thermal stability of the immunogenic composition, compatibility of the immunogenic composition with the container/closure system, interactions between immunogenic composition and inactive ingredients (e.g., buffers, salts, excipients, cryoprotectants), manufacturing processes, dosage form, environmental conditions encountered during shipping, storage and handling (e.g., temperature, humidity, shear forces), and the length of time between manufacture and usage.

The stability of an immunogenic composition of the invention is readily determined using standard techniques, which are well known and routine to those of skill in the art. For example, an immunogenic composition is assayed for stability, aggregation, immunogenicity, particulate formation, protein (concentration) loss, and the like, by methods including, but not limited to, light scattering, optical density, sedimentation velocity centrifugation, sedimentation equilibrium centrifugation, circular dichroism (CD), Lowry assay, bicinchoninic acid (BCA) assay, antibody binding, and the like.

As set forth in detail herein, the present invention relates to the unexpected and surprising results that formulating an immunogenic composition with a surfactant such as Tween™80 significantly enhances the stability and inhibits precipitation of an immunogenic composition. For example, it was observed in the present invention (e.g., see Example 2), that a thirteen-valent pneumococcal conjugate (13vPnC), formulated in buffered saline and filled in a single does syringe, would begin precipitating out of solution within ten minutes at 2-8° C. upon gentle agitation via a horizontal orbital shaker. (The horizontal orbital shaker was used to simulate typical process, shipping and storage conditions of a 13vPnC immunogenic composition). However, it was surprisingly observed that the 13vPnC, formulated in buffered saline and 0.001% Tween™80, filled in a single dose syringe and gently agitated at 2-8° C., was stable for twenty-five days with no visible signs of precipitation (data not shown). Thus, this data demonstrated that the addition of a surfactant (e.g., Tween™80) to an immunogenic composition formulation enhances the stability of the immunogenic composition.

A second stability study of the 13vPnC further confirmed that the addition of a surfactant to the formulation significantly enhanced the stability of the 13vPnC. For example, the stability (i.e., assayed by measuring change in 13vPnC antigenicity) of a 13vPnC formulation with 0.05% Tween™80 (Table 1) and without Tween™80 (0.0%, Table 1) was assessed over a two hour time period. As is shown in Table 1, there was a significant decrease in antigenicity of the thirteen serotype polysaccharides (formulated without Tween™80) within the two hour assay. Quite dramatically however, the 13vPnC formulation comprising 0.05% Tween™80 (Table 1), demonstrated robust stability throughout the two hour antigenicity assay. It was also observed that the 13vPnC formulated in 250 mL glass bottles with either 0.01% Tween™80 or 0.05% Tween™80 could withstand significant shear forces induced via vortexing the formulations for thirty minutes at 2-8° C., with little or no loss in antigenicity (e.g., see Example 2, Table 2).

In other experiments (Example 3), it was demonstrated that the stability of an immunogenic streptococcal C5a peptidase (SCP) composition was greatly enhanced when formulated with a surfactant such as Tween™80. For example, as shown in FIG. 1A, after two days of vortexing an SCP (55 µg/mL) formulated in either a 5 mM succinate buffer (pH 6.0), a 10 mM phosphate buffer (pH 7.0 and 7.4) or a 10 mM Tris buffer (pH 7.5), there was a significant decrease (e.g., greater than 90%) in the SCP concentration. However, as shown in FIG. 1 B, the addition of 0.025% Tween™80 to the SCP succinate, SCP phosphate and SCP Tris formulations, prior to vortexing for two days, completely inhibited the SCP loss which was observed in FIG. 1A.

A 13vPnC immunogenic composition of the invention may also be formulated with or without an adjuvant, such as aluminum phosphate ($AlPO_4$). Thus, in a separate series of experiments (Example 4), 13vPnC immunogenic compositions were formulated in 5 mM succinate buffer (pH 5.8), 0.85% NaCl and $AlPO_4$ (0.25 mg aluminum/ml), without the addition of a surfactant (e.g., no Tween™80 was included in the formulation).

In these experiments, the 13vPnC immunogenic composition (formulated in the presence of $AlPO_4$) were filled in various siliconized and non-siliconized container means (e.g., see Table 3) and subjected to simulated shipping and handling conditions via agitation at 2-8° C. It was observed in these experiments (Example 4), that the container means with higher silicone content exhibited a higher degree of 13vPnC particulate formation and a higher percent of 13vPnC antigenicity loss. An FTIR analysis of the particulates indicated that the particulates consisted of protein and silicone (data not shown) and that about 85% of the 13vPnC is bound to the $AlPO_4$, wherein the remaining 15% was free (not bound to $AlPO_4$) 13vPnC in solution.

Figure 6A:
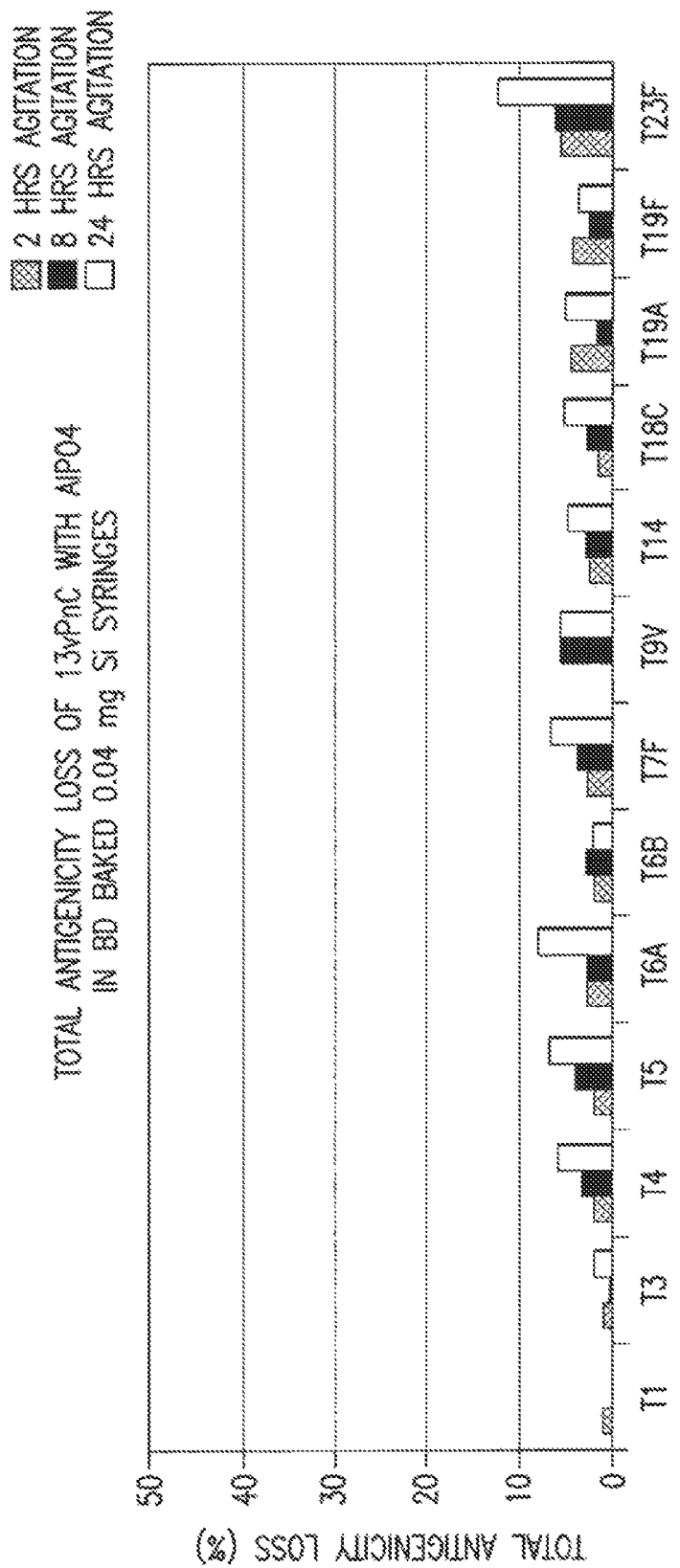
FIG. 6 shows the total antigenicity loss of the 13vPnC formulated with (FIG. 6A) and without (FIG. 6B) $AlPO_4$ (0.25 mg/ml) and filled in a BD Baked syringe, after two hours, eight hours and twenty-four hours of agitation at 500 rpm and 2-8° C.
Figure 6B:
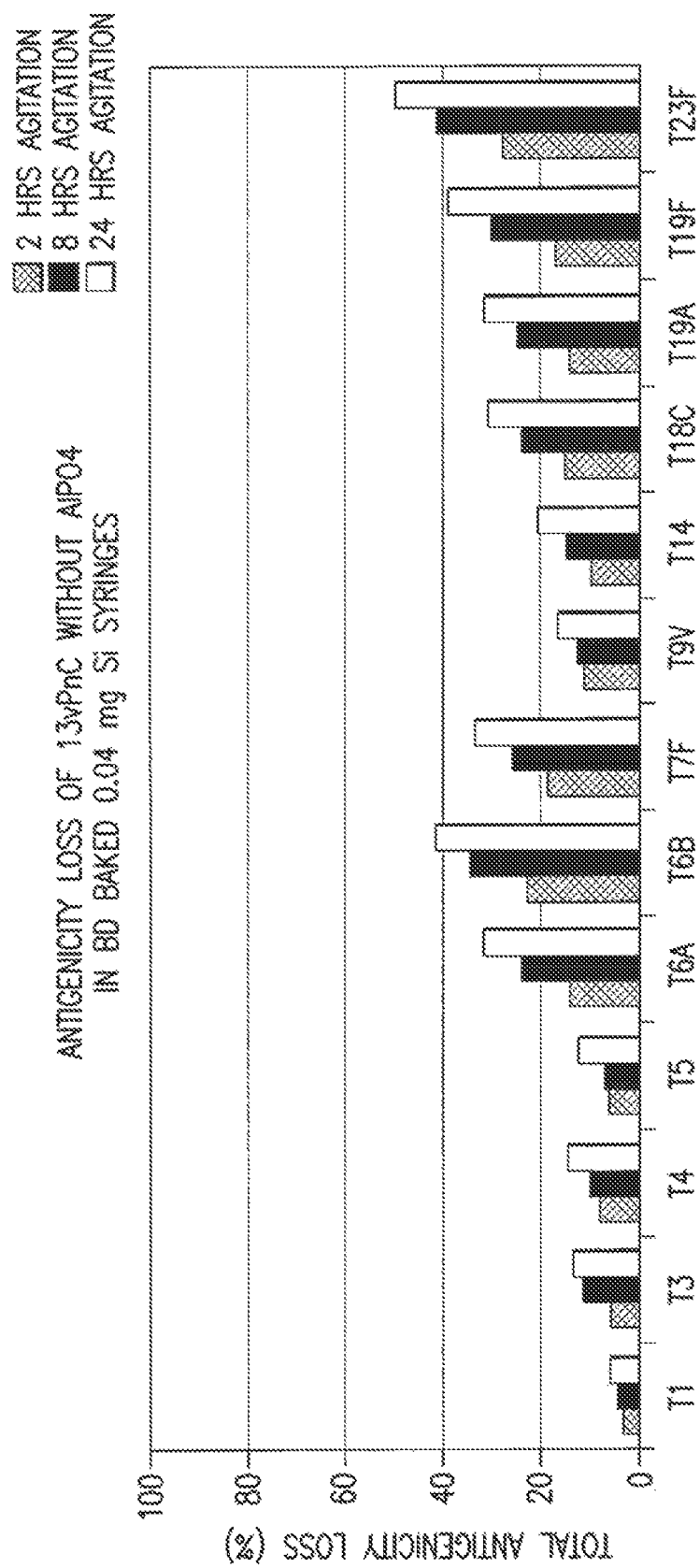
Figure 7B:
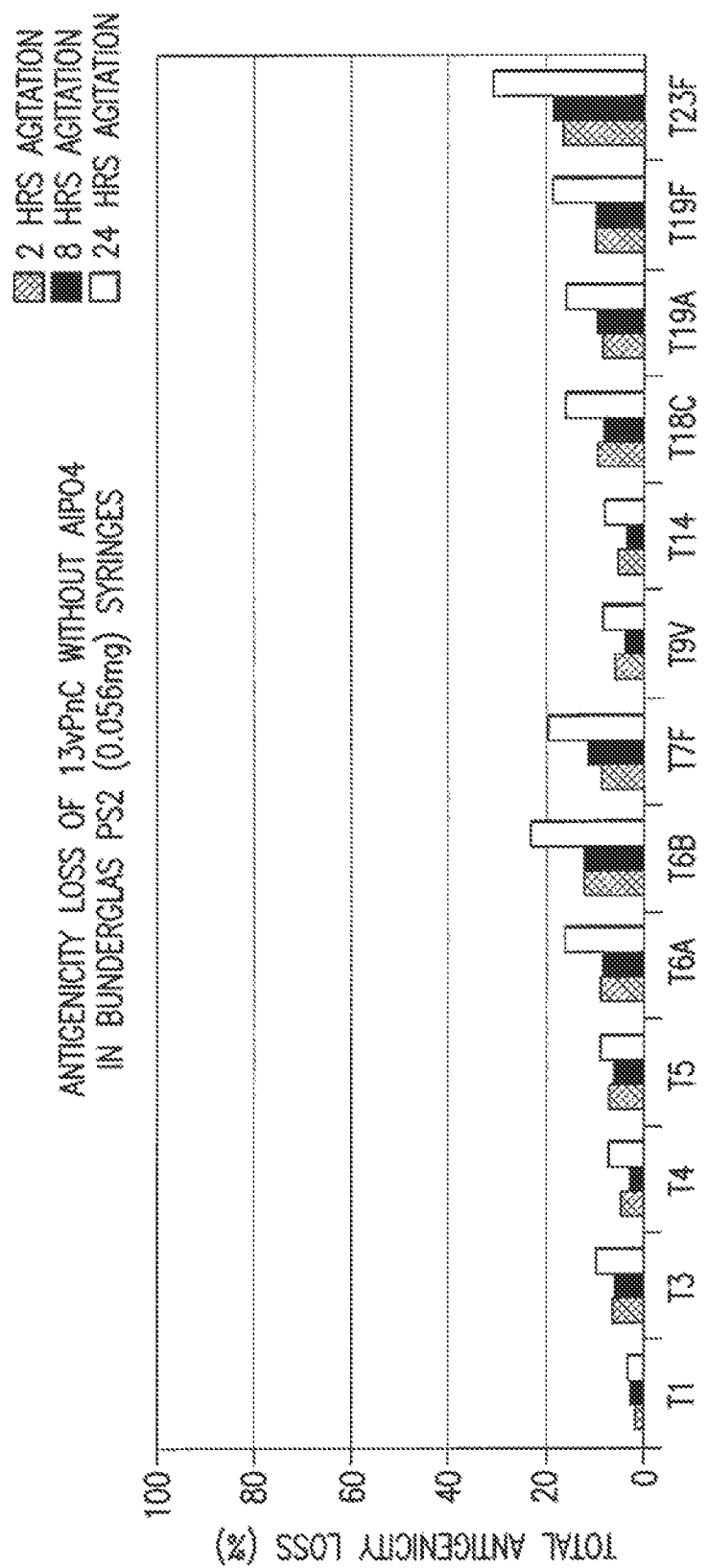
FIG. 7 shows the total antigenicity loss of the 13vPnC formulated with (FIG. 7A) and without (FIG. 7B) $AlPO_4$ (0.25 mg/ml) and filled in a BünderGlas PS2 syringe, after two hours, eight hours and twenty-four hours of agitation at 500 rpm and 2-8° C.

In another experiment comparing 13vPnC immunogenic compositions formulated with and without $AlPO_4$, which were then filled in identical syringes, it was observed that the 13vPnC formulated without $AlPO_4$ sustained greater antigenicity losses than 13vPnC with $AlPO_4$ in the syringes tested (e.g., see FIG. 6 and FIG. 7).

Thus, the invention as set forth herein, is directed to novel formulations which stabilize and inhibit aggregation or precipitation of immunogenic compositions such as polysaccharide-protein conjugates (e.g., a 13vPnC) and protein immunogens (e.g., a streptococcal C5a peptidase, a N. meningitidis ORF 2086 protein), against the various factors which influence the stability of immunogenic compositions (e.g., shear forces, shipping agitation, silicone oil interactions, adsorption, manufacturing processes, temperature, humidity, length of time between manufacture and usage, etc.).

In certain embodiments, the invention is directed to a formulation which stabilizes a polysaccharide-protein conjugate, the formulation comprising a pH buffered saline solution, wherein the buffer has a pKa of about 3.5 to about 7.5, a surfactant and one or more polysaccharide-protein conjugates. In other embodiments, the polysaccharide-protein conjugate formulation is comprised in a container means. In another embodiment, the invention is directed to a formulation which stabilizes a streptococcal C5a peptidase (SCP) composition, the formulation comprising a pH buffered saline solution, wherein the buffer has a pKa of about 3.5 to about 6.5, a surfactant and a streptococcal C5a peptidase. In certain embodiments, the SCP formulation is comprised in a container means. In another embodiment, the invention is directed to a formulation which stabilizes a N. meningitidis 2086 protein composition, the formulation comprising a pH buffered saline solution, wherein the buffer has a pKa of about 3.5 to about 7.5, a surfactant and a N. meningitidis 2086 protein. In certain embodiments, the meningococcal 2086 formulation is comprised in a container means.

In certain other embodiments, the invention is directed to a formulation which inhibits silicone induced precipitation of a polysaccharide-protein conjugate comprised in a siliconized container means, the formulation comprising a pH buffered saline solution, wherein the buffer has a pKa of about 3.5 to about 7.5, an aluminum salt and one or more polysaccharide-protein conjugates. In another embodiment, the invention is directed to a formulation which inhibits silicone induced precipitation of a streptococcal C5a peptidase (SCP) composition comprised in a siliconized container means, the formulation comprising a pH buffered saline solution, wherein the buffer has a pKa of about 3.5 to about 6.5, an aluminum salt and a streptococcal C5a peptidase. In certain other embodiments, the invention is directed to a formulation which inhibits silicone induced precipitation of a N. meningitidis 2086 protein composition comprised in a siliconized container means, the formulation comprising a pH buffered saline solution, wherein the buffer has a pKa of about 3.5 to about 7.5, an aluminum salt and a N. meningitidis 2086 protein.

In yet other embodiments, the invention is directed to a formulation that optimizes antigen stability and binding percentage to an aluminum salt adjuvant (e.g., $AlPO_4$) of a N. meningitidis 2086 protein, the formulation comprising a pH buffered saline solution, wherein the buffer has a pKa of about 3.5 to about 7.5, a surfactant, an aluminum salt, and a N. meningitidis 2086 protein. In certain embodiments, the formulation is in a container means.

As defined hereinafter, the terms "precipitation", "precipitate" "particulate formation", "clouding" and "aggregation" may be used interchangeably and are meant to refer to any physical interaction or chemical reaction which results in the "aggregation" of a polysaccharide-protein conjugate or a protein (or polypeptide) immunogen. The process of aggregation (e.g., protein aggregation) is well known (but not well understood) and described in the art, and is often influenced by numerous physicochemical stresses, including heat, pressure, pH, agitation, shear forces, freeze-thawing, dehydration, heavy metals, phenolic compounds, silicon oil, denaturants and the like.

As defined hereinafter, a "polysaccharide-protein conjugate", a "pneumococcal conjugate", a "7-valent pneumococcal conjugate (7vPnC)", a "13-valent pneumococcal conjugate (13vPnC)", a "streptococcal C5a peptidase (SCP) immunogenic composition" and a "N. meningitidis 2086 protein immunogenic composition" of the invention includes liquid formulations, frozen liquid formulations and solid (e.g., freeze-dried or lyophilized) formulations.

A. Surfactants

As set forth above, the invention is directed to formulations which stabilize and inhibit aggregation of immunogenic compositions against the various factors which influence the stability of immunogenic compositions (e.g., shear forces, shipping agitation, silicone oil interactions, adsorption, manufacturing processes, temperature, humidity, length of time between manufacture and usage, etc.). In certain embodiments, the invention is directed to formulations comprising a surfactant.

A surfactant (or a surface-active agent) is generally defined as (a) a molecule or compound comprising a hydrophilic group or moiety and a lipophilic (hydrophobic) group or moiety and/or (b) a molecule, substance or compound that lowers or reduces surface tension of a solution. As defined herein, a "surfactant" of the present invention is any molecule or compound that lowers the surface tension of an immunogenic composition formulation.

A surfactant used in a formulation of the present invention comprises any surfactant or any combination of surfactants which stabilizes and inhibits aggregation of an immunogenic composition described herein. Thus, a surfactant of the invention includes, but is not limited to, polysorbate 20 (Tween™20), polysorbate 40 (Tween™40), polysorbate 60 (Tween™60), polysorbate 65 (Tween™65), polysorbate 80 (Tween™80), polysorbate 85 (Tween™85), Triton™ N-101, Triton™ X-100, oxtoxynol 40, nonoxynol-9, triethanolamine, triethanolamine polypeptide oleate, polyoxyethylene-660 hydroxystearate (PEG-15, Solutol H15), polyoxyethylene-35-ricinoleate (Cremophor EL™), soy lecithin, poloxamer, hexadecylamine, octadecylamine, octadecyl amino acid esters, lysolecithin, dimethyl-dioctadecylammonium bromide, methoxyhexadecylgylcerol, pluronic polyols, polyamines (e.g., pyran, dextransulfate, poly IC, carbopol), peptides (e.g., muramyl peptide and dipeptide, dimethylglycine, tuftsin), oil emulsions, mineral gels (e.g., aluminum phosphate) and immune stimulating complexes (ISCOMS).

A person of skill in the art may readily determine a suitable surfactant or surfactant combination by measuring the surface tension of a particular immunogenic composition formulation in the presence and absence of the surfactant(s). Alternatively, a surfactant is evaluated qualitatively (e.g., visual inspection of particulate formation) or quantitatively (e.g., light scattering, sedimentation velocity centrifugation, optical density, antigenicity) for its ability to reduce, inhibit or prevent aggregation of an immunogenic composition.

B. Container Means

In certain embodiments, the invention is directed to formulations of immunogenic compositions comprised in a container means. As defined herein, a "container means" of the present invention includes any composition of matter which is used to "contain", "hold", "mix", "blend", "dispense", "inject", "transfer", "nebulize", etc. an immunogenic composition during research, processing, development, formulation, manufacture, storage and/or administration. For example, a container means of the present invention includes, but is not limited to, general laboratory glassware, flasks, beakers, graduated cylinders, fermentors, bioreactors, tubings, pipes, bags, jars, vials, vial closures (e.g., a rubber stopper, a screw on cap), ampoules, syringes, syringe stoppers, syringe plungers, rubber closures, plastic closures, glass closures, and the like. A container means of the present invention is not limited by material of manufacture, and includes materials such as glass, metals (e.g., steel, stainless steel, aluminum, etc.) and polymers (e.g., thermoplastics, elastomers, thermoplastic-elastomers).

The skilled artisan will appreciate that the container means set forth above are by no means an exhaustive list, but merely serve as guidance to the artisan with respect to the variety of container means which are used to contain, hold, mix, blend, dispense, inject, transfer, nebulize, etc. an immunogen or immunogenic composition during research, processing, development, formulation, manufacture, storage and/or administration of the composition. Additional container means contemplated for use in the present invention may be found in published catalogues from laboratory equipment vendors and manufacturers such as United States Plastic Corp. (Lima, Ohio), VWR™ (West Chester, Pa.), BD Biosciences (Franklin Lakes, N.J.), Fisher Scientific International Inc. (Hampton, N.H.) and Sigma-Aldrich (St. Louis, Mo.).

Thus, the novel formulations of the present invention are particularly advantageous in that they stabilize and inhibit precipitation of immunogenic formulations comprised in a container means throughout the various stages of research, processing, development, formulation, manufacture, storage and/or administration of the composition. The novel formulations of the invention not only stabilize immunogenic compositions against physical/thermal stresses (e.g., temperature, humidity, shear forces, etc.), they also enhance stability and inhibit precipitation of immunogenic compositions against negative factors or influences such as incompatibility of the immunogenic composition with the container/closure system (e.g., a siliconized container means).

Thus, the novel formulations of the present invention are particularly useful in stabilizing the immunogen (i.e., a polysaccharide-protein conjugate, a protein or polypeptide antigen) against the silicon oil induced precipitation and precipitation described above. For example, co-pending U.S. Application No. 60/795,098, filed Apr. 26, 2006, specifically incorporated herein by reference, describes the aggregation of immunogenic compositions in the presence silicon oil found on container means such syringes, glass vials, rubbers stoppers and the like, wherein the addition of a surfactant to the container means prevented the silicon oil induced aggregation of these immunogenic compositions.

C. Adjuvants and Pharmaceutical Carriers/Excipients

In certain embodiments, the immunogenic compositions of the invention are further formulated with an adjuvant. An adjuvant is a substance that enhances the immune response when administered together with an immunogen or antigen. A number of cytokines or lymphokines have been shown to have immune modulating activity, and thus may be used as adjuvants, including, but not limited to, the interleukins 1-α, 1-β, 2, 4, 5, 6, 7, 8, 10, 12 (see, e.g., U.S. Pat. No. 5,723,127), 13, 14, 15, 16, 17 and 18 (and its mutant forms), the interferons-α, β and γ, granulocyte-macrophage colony stimulating factor (GMCSF, see, e.g., U.S. Pat. No. 5,078,996 and ATCC Accession Number 39900), macrophage colony stimulating factor (MCSF), granulocyte colony stimulating factor (GCSF), and the tumor necrosis factors α and β (TNF). Still other adjuvants useful in this invention include chemokines, including without limitation, MCP-1, MIP-1α, MIP-1β, and RANTES.

In certain embodiments, an adjuvant used to enhance an immune response of an immunogenic composition formulation includes, without limitation, MPL™ (3-O-deacylated monophosphoryl lipid A; Corixa, Hamilton, Mont.), which is described in U.S. Pat. No. 4,912,094, which is hereby incorporated by reference. Also suitable for use as adjuvants are synthetic lipid A analogs or aminoalkyl glucosamine phosphate compounds (AGP), or derivatives or analogs thereof, which are available from Corixa (Hamilton, Mont.), and which are described in U.S. Pat. No. 6,113,918, which is hereby incorporated by reference. One such AGP is 2-[(R)-3-Tetradecanoyloxytetradecanoylamino]ethyl 2-Deoxy-4-O-phosphono-3-O—[(R)-3-tetradecanoyoxytetradecanoyl]-2-[(R)-3-tetradecanoyloxytetradecanoyl-amino]-b-D-glucopyranoside, which is also known as 529 (formerly known as RC529). This 529 adjuvant is formulated as an aqueous form or as a stable emulsion (RC529-SE).

Still other adjuvants include mineral oil and water emulsions, aluminum salts (alum), such as aluminum hydroxide, aluminum phosphate, aluminum sulfate etc., Amphigen, Avridine, L121/squalene, D-lactide-polylactide/glycoside, pluronic polyols, muramyl dipeptide, killed *Bordetella*, saponins, such as Stimulon™ QS-21 (Antigenics, Framingham, Mass.), described in U.S. Pat. No. 5,057,540, which is hereby incorporated by reference, and particles generated therefrom such as ISCOMS (immunostimulating complexes), ISCOMATRIX (CSL Limited, Parkville, Australia), described in U.S. Pat. No. 5,254,339, Mycobacterium tuberculosis, bacterial lipopolysaccharides, synthetic polynucleotides such as oligonucleotides containing a CpG motif (U.S. Pat. No. 6,207,646, which is hereby incorporated by reference), IC-31 (Intercell AG, Vienna, Austria), described in European Patent Nos. 1,296,713 and 1,326,634, a pertussis toxin (PT), or an *E. coli* heat-labile toxin (LT), particularly LT-K63, LT-R72, PT-K9/G129; see, e.g., International Patent Publication Nos. WO 93/13302 and WO 92/19265, incorporated herein by reference.

Also useful as adjuvants (and carrier proteins) are cholera toxins and mutants thereof, including those described in published International Patent Application number WO 00/18434 (wherein the glutamic acid at amino acid position 29 is replaced by another amino acid (other than aspartic acid), preferably a histidine). Similar CT toxins or mutants are described in published International Patent Application number WO 02/098368 (wherein the isoleucine at amino acid position 16 is replaced by another amino acid, either alone or in combination with the replacement of the serine at amino acid position 68 by another amino acid; and/or wherein the valine at amino acid position 72 is replaced by another amino acid). Other CT toxins are described in published International Patent Application number WO 02/098369 (wherein the arginine at amino acid position 25 is replaced by another amino acid; and/or an amino acid is inserted at amino acid position 49; and/or two amino acids are inserted at amino acid positions 35 and 36).

In certain embodiments, the immunogenic composition formulations comprise a pharmaceutically acceptable diluent, excipient or a pharmaceutically acceptable carrier. In one embodiment, the pharmaceutically acceptable diluent is sterile water, water for injection, sterile isotonic saline or a biological buffer. The polysaccharide-protein conjugates and/or protein immunogens are mixed with such diluents or carriers in a conventional manner. As used herein the language "pharmaceutically acceptable carrier" is intended to include any and all solvents, dispersion media, coatings, antibacterial and antifungal agents, isotonic and absorption delaying agents, and the like, compatible with administration to humans or other vertebrate hosts. The appropriate carrier is evident to those skilled in the art and will depend in large part upon the route of administration.

For example, excipients that may be present in the immunogenic composition formulation are preservatives, chemical stabilizers and suspending or dispersing agents. Typically, stabilizers, preservatives and the like are optimized to determine the best formulation for efficacy in the targeted recipient (e.g., a human subject). Examples of preservatives include chlorobutanol, potassium sorbate, sorbic acid, sulfur dioxide, propyl gallate, the parabens, ethyl vanillin, glycerin, phenol, and parachlorophenol. Examples of stabilizing ingredients include casamino acids, sucrose, gelatin, phenol red, N—Z amine, monopotassium diphosphate, lactose, lactalbumin hydrolysate, and dried milk.

In certain embodiments, an immunogenic composition formulation is prepared for administration to human subjects in the form of, for example, liquids, powders, aerosols, tablets, capsules, enteric-coated tablets or capsules, or suppositories. Thus, the immunogenic composition formulations may also include, but are not limited to, suspensions, solutions, emulsions in oily or aqueous vehicles, pastes, and implantable sustained-release or biodegradable formulations.

The immunogenic compositions of the present invention, are not limited by the selection of the conventional, physiologically acceptable carriers, diluents and excipients such as solvents, buffers, adjuvants, or other ingredients useful in pharmaceutical preparations of the types described above. The preparation of these pharmaceutically acceptable compositions, from the above-described components, having appropriate pH isotonicity, stability and other conventional characteristics is within the skill of the art.

D. Immunogens

In certain embodiments, a polysaccharide-protein conjugate formulation of the invention comprises one or more pneumococcal polysaccharides. In other embodiments, a polysaccharide-protein conjugate formulation of the invention comprises one or more streptococcal polysaccharides. In yet other embodiments, a polysaccharide-protein conjugate formulation of the invention comprises one or more meningococcal polysaccharides. In still other embodiments, a polysaccharide-protein conjugate formulation of the invention comprises a combination of one or more pneumococcal polysaccharides, one or more pneumococcal polypeptides, one or more streptococcal polysaccharides, one or more streptococcal polypeptides, one or more meningococcal polysaccharides, and/or one or more meningococcal polypeptides.

As defined hereinafter, the term "polysaccharide" is meant to include any antigenic saccharide element (or antigenic unit) commonly used in the immunologic and bacterial vaccine arts, including, but not limited to, a "saccharide", an "oligosaccharide", a "polysaccharide", a "liposaccharide", a "lipo-oligosaccharide (LOS)", a "lipopolysaccharide (LPS)", a "glycosylate", a "glycoconjugate" and the like.

In one particular embodiment of the invention, the one or more pneumococcal polysaccharides are a *S. pneumoniae* serotype 4 polysaccharide, a *S. pneumoniae* serotype 6B polysaccharide, a *S. pneumoniae* serotype 9V polysaccharide, a *S. pneumoniae* serotype 14 polysaccharide, a *S. pneumoniae* serotype 18C polysaccharide, a *S. pneumoniae* serotype 19F polysaccharide, a *S. pneumoniae* serotype 23F polysaccharide, a *S. pneumoniae* serotype 1 polysaccharide, a *S. pneumoniae* serotype 3 polysaccharide, a *S. pneumoniae* serotype 5 polysaccharide, a *S. pneumoniae* serotype 6A polysaccharide, a *S. pneumoniae* serotype 7F polysaccharide and a *S. pneumoniae* serotype 19A polysaccharide.

In certain embodiments, a polysaccharide-protein conjugate formulation is a 7-valent pneumococcal conjugate (7vPnC) formulation comprising a *S. pneumoniae* serotype 4 polysaccharide conjugated to a $CRM_{197}$ polypeptide, a *S. pneumoniae* serotype 6B polysaccharide conjugated to a $CRM_{197}$ polypeptide, a *S. pneumoniae* serotype 9V polysaccharide conjugated to a $CRM_{197}$ polypeptide, a *S. pneumoniae* serotype 14 polysaccharide conjugated to a $CRM_{197}$ polypeptide, a *S. pneumoniae* serotype 18C polysaccharide conjugated to a $CRM_{197}$ polypeptide, a *S. pneumoniae* serotype 19F polysaccharide conjugated to a $CRM_{197}$ polypeptide and a *S. pneumoniae* serotype 23F polysaccharide conjugated to a $CRM_{197}$ polypeptide.

In certain other embodiments, a polysaccharide-protein conjugate formulation is a 13-valent pneumococcal conjugate (13vPnC) formulation comprising a *S. pneumoniae* serotype 4 polysaccharide conjugated to a $CRM_{197}$ polypeptide, a S. pneumoniae serotype 6B polysaccharide conjugated to a $CRM_{197}$ polypeptide, a S. pneumoniae serotype 9V polysaccharide conjugated to a $CRM_{197}$ polypeptide, a S. pneumoniae serotype 14 polysaccharide conjugated to a $CRM_{197}$ polypeptide, a S. pneumoniae serotype 18C polysaccharide conjugated to a $CRM_{197}$ polypeptide, a S. pneumoniae serotype 19F polysaccharide conjugated to a $CRM_{197}$ polypeptide, a S. pneumoniae serotype 23F polysaccharide conjugated to a $CRM_{197}$ polypeptide, a S. pneumoniae serotype 1 polysaccharide conjugated to a $CRM_{197}$ polypeptide, a S. pneumoniae serotype 3 polysaccharide conjugated to a $CRM_{197}$ polypeptide, a S. pneumoniae serotype 5 polysaccharide conjugated to a $CRM_{197}$ polypeptide, a S. pneumoniae serotype 6A polysaccharide conjugated to a $CRM_{197}$ polypeptide, a S. pneumoniae serotype 7F polysaccharide conjugated to a $CRM_{197}$ polypeptide and a S. pneumoniae serotype 19A polysaccharide conjugated to a $CRM_{197}$ polypeptide.

Polysaccharides are prepared by standard techniques known to those skilled in the art. For example, the capsular polysaccharides set forth in the present invention are prepared from serotypes 1, 3, 4, 5, 6A, 6B, 7F, 9V, 14, 18C, 19A, 19F and 23F of Streptococcus pneumoniae, wherein each serotype is grown in a soy-based medium and the individual polysaccharides are then purified through centrifugation, precipitation, ultra-filtration, and column chromatography. Similarly, streptococcal polysaccharides (e.g., one or more polysaccharides (or oligosaccharides) from a (3-hemolytic Streptococcus such group A Streptococcus, group B Streptococcus, group C Streptococcus and group G Streptococcus) and meningococcal saccharides (e.g., an N. meningitidis lipo-oligosaccharide (LOS) or lipo-polysaccharide (LPS)) are prepared from clinically relevant serotypes or serogroups, using general techniques and methods known to one of skill in the art. The purified polysaccharides are then chemically activated (e.g., via reductive amination) to make the saccharides capable of reacting with the carrier protein. Once activated, each capsular polysaccharide is separately conjugated to a carrier protein (e.g., $CRM_{197}$) to form a glycoconjugate (or alternatively, each capsular polysaccharide is conjugated to the same carrier protein) and formulated into a single dosage formulation.

The chemical activation of the polysaccharides and subsequent conjugation to the carrier protein (i.e., a polysaccharide-protein conjugate) are achieved by conventional means. See, for example, U.S. Pat. Nos. 4,673,574 and 4,902,506.

Carrier proteins are preferably proteins that are non-toxic and non-reactogenic and obtainable in sufficient amount and purity. Carrier proteins should be amenable to standard conjugation procedures. In a particular embodiment of the present invention, $CRM_{197}$ is used as the carrier protein.

$CRM_{197}$ (Wyeth, Sanford, N.C.) is a non-toxic variant (i.e., toxoid) of diphtheria toxin isolated from cultures of Corynebacterium diphtheria strain C7 (β197) grown in casamino acids and yeast extract-based medium. $CRM_{197}$ is purified through ultra-filtration, ammonium sulfate precipitation, and ion-exchange chromatography. Alternatively, $CRM_{197}$ is prepared recombinantly in accordance with U.S. Pat. No. 5,614,382, which is hereby incorporated by reference. Other diphtheria toxoids are also suitable for use as carrier proteins.

In other embodiments, a carrier protein of the invention is an enzymatically inactive streptococcal C5a peptidase (SCP) (e.g., one or more of the SCP variants described in U.S. Pat. Nos. 6,951,653, 6,355,255 and 6,270,775).

Other suitable carrier proteins include inactivated bacterial toxins such as tetanus toxoid, pertussis toxoid, cholera toxoid (e.g., CT E29H, described in International Patent Application WO2004/083251), E. coli LT, E. coli ST, and exotoxin A from Pseudomonas aeruginosa. Bacterial outer membrane proteins such as outer membrane complex c (OMPC), porins, transferrin binding proteins, pneumolysin, pneumococcal surface protein A (PspA), pneumococcal adhesin protein (PsaA), or Haemophilus influenzae protein D, can also be used. Other proteins, such as ovalbumin, keyhole limpet hemocyanin (KLH), bovine serum albumin (BSA) or purified protein derivative of tuberculin (PPD) can also be used as carrier proteins.

After conjugation of the capsular polysaccharide to the carrier protein, the polysaccharide-protein conjugates are purified (enriched with respect to the amount of polysaccharide-protein conjugate) by a variety of techniques. These techniques include concentration/diafiltration operations, precipitation/elution, column chromatography, and depth filtration.

After the individual glycoconjugates are purified, they are compounded to formulate the immunogenic composition of the present invention. Formulation of the polysaccharide-protein conjugates of the present invention can be accomplished using art-recognized methods. For instance, the 13 individual pneumococcal conjugates can be formulated with a physiologically acceptable vehicle to prepare the composition. Examples of such vehicles include, but are not limited to, water, buffered saline, polyols (e.g., glycerol, propylene glycol, liquid polyethylene glycol) and dextrose solutions.

In other embodiments, the invention is directed to formulations which stabilize a streptococcal C5a peptidase (SCP) immunogenic composition, wherein the formulations comprise a pH buffered saline solution, wherein the buffer has a pKa of about 3.5 to about 6.5, a surfactant and a streptococcal C5a peptidase. The C5a peptidase is a highly conserved serine protease and is expressed across all β-hemolytic Streptococci (e.g., streptococcal Groups A, B, C and G). For example, the nucleotide sequence encoding a Group B streptococci (GBS) C5a peptidase is 98% identical to the nucleotide sequence encoding a Group A streptococci (GAS) C5a peptidase. Thus, in certain embodiments of the invention, an immunogenic composition against infection caused by β-hemolytic Streptococci comprises a C5a peptidase immunogen (or antigen).

In one particular embodiment, a C5a peptidase of the invention is an enzymatically inactive streptococcal C5a peptidase (e.g., one or more of the SCP variants described in U.S. Pat. Nos. 6,951,653, 6,355,255 and 6,270,775, each specifically incorporated herein by reference). In another specific embodiment, the SCP used in the novel immunogenic composition formulations of the invention is cloned from a Group B streptococci. In another embodiment, the Group B streptococci SCP sequence has been genetically mutated to render it proteolytically inactive (e.g., see U.S. Pat. Nos. 6,951,653; 6,355,255 and 6,270,775) and is expressed as a recombinant protein in E. coli.

In another embodiment, the invention is directed to formulations which stabilize a N. meningitidis 2086 protein immunogenic composition, wherein the formulations comprise a pH buffered saline solution, wherein the buffer has a pKa of about 3.5 to about 7.5, a surfactant and a N. meningitidis 2086 protein. The N. meningitidis 2086 proteins are encoded by a nucleic acid sequence open reading frame (ORF) identified as "ORF 2086" (e.g., see International Publication No. WO 03/063766 A2 (International Application No. PCT/US02/32369), International Publication No. WO 04/094596 A2 (International Application No. PCT/US04/011901), and International Publication No. WO 04/065603 A2 (International Application No. PCT/US04/000800), each specifically incorporated herein by reference). In a further embodiment, the invention is directed to formulations that optimize antigen stability and binding percentage to an aluminum salt adjuvant (e.g., $AlPO_4$) of a *N. meningitidis* 2086 protein, wherein the formulations comprise a pH buffered saline solution, wherein the buffer has a pKa of about 3.5 to about 7.5, a surfactant, an aluminum salt, and a *N. meningitidis* 2086 protein.

All patents and publications cited herein are hereby incorporated by reference.

E. Examples

The following examples are carried out using standard techniques, which are well known and routine to those of skill in the art, except where otherwise described in detail. The following examples are presented for illustrative purpose, and should not be construed in any way as limiting the scope of this invention.

Example 1

Immunogenic Formulations Comprising 0.001%-0.05% Tween™80 Stabilize and Prevent Aggregation of the Immunogen The polysaccharide-protein conjugate used in this example was a thirteen-valent pneumococcal polysaccharide conjugate (13vPnC) comprising capsular polysaccharides from *S. pneumoniae* serotypes 4, 6B, 9V, 18C, 19F, 14, 23F, 1, 3, 5, 6A, 7F and 19A, each of which were conjugated to $CRM_{197}$. The capsular polysaccharides were prepared by standard techniques known to those skilled in the art. Briefly, each pneumococcal polysaccharide serotype was grown in a soy-based medium, the individual polysaccharides were then purified through centrifugation, precipitation, ultra-filtration, and column chromatography. The purified polysaccharides were chemically activated for conjugation and each polysaccharide was separately conjugated to a $CRM_{197}$ carrier protein to form a glycoconjugate and formulated into a single dosage formulation.

The chemical activation of the polysaccharides and subsequent conjugation to the carrier protein were achieved by conventional means (e.g., see U.S. Pat. Nos. 4,673,574 and 4,902,506). $CRM_{197}$ (Wyeth, Sanford, N.C.) is a non-toxic variant (i.e., toxoid) of diphtheria toxin isolated from cultures of *Corynebacterium diphtheria* strain C7 (β197) grown in casamino acids and yeast extract-based medium. $CRM_{197}$ is purified through ultra-filtration, ammonium sulfate precipitation, and ion-exchange chromatography.

The antigenicity experiments described below were performed by mixing the 13vPnC samples with one of thirteen antisera (Ab) specific to the each of the polysaccharide serotypes and detecting the immune complexes via light scattering measurements on an Array® 360 system (Beckman Coulter, Inc.; Fullerton, Calif.). The detected light scattering measurements for each of the thirteen serotypes were then compared to a standard curve and reported as antigenicity (µg/mL).

Syringes (BD Hypak SCF™) and syringe stoppers (BD Hypak SCF™) were purchased from BD Biosciences (Franklin Lakes, N.J.). Clear borosilicate vials (VWR Trace-Clean™, 40 mL) with Teflon®-lined closures were purchased from VWR™ (West Chester, Pa.). Polysorbate 80 (Tween™80) was purchased from J.T. Baker (Mallinckrodt Baker, Inc.; Phillipsburg, N.J.). Buffered saline was succinate (5 mM) and NaCl (0.85%) at pH 5.8.

The 13vPnC was formulated (500 mL total volume) at different surfactant concentrations (Tween™80; 0.001%, 0.005%, 0.01% and 0.05%, weight/volume) as follows: 0.85% saline (150 mM NaCl) was added to a one liter Pyrex® glass beaker, followed by 50 mM succinate buffer (final concentration 5 mM) and the 13vPnC. The final concentration of each serotype conjugate was 4.4 µg/mL (except for serotype 6B, which was 8.8 µg/mL). The 13vPnC formulation was then divided into five separate glass vials (50 mL per vial), wherein either 0.0%, 0.001%, 0.005%, 0.01% or 0.05% Tween™80 (w/v) was added to one of the five vials and each solution filtered through a 0.22 µm Durapore® filter (Millipore; Billerica, Mass.). Subsequently, 0.65 mL of each solution was filled in a separate 3 mL BD HYPAK™ SCF™ glass syringe with w4432 grey stoppers (BD Medical Pharmaceutical Systems; Franklin Lakes, N.J.), and the syringes placed on a horizontal orbital shaker (60 cpm) for 100 hours at 2° C. to 8° C.

It was observed by visual inspection (data not shown), that the 13vPnC formulated in the absence of Tween™80 (i.e., 0.0%), would begin precipitating out of solution within ten minutes at 2-8° C. upon gentle agitation via a horizontal orbital shaker. In contrast, the 13vPnC, formulated in 0.001%, 0.005%, 0.01% or 0.05% Tween™80 and gently agitated at 2-8° C., was stable for up to twenty-five days with no visible signs of precipitation (data not shown). Thus, this data demonstrated that the addition of a surfactant (e.g., Tween™80) to an immunogenic composition formulation enhances the stability of the immunogenic composition.

A second stability experiment of the 13vPnC further confirmed that the addition of surfactant to the formulation significantly enhanced the stability of the 13vPnC. In this experiment, the 13vPnC was formulated with and without 0.05% Tween™80. The 13vPnC formulated without Tween™80 (i.e., 0.0%) was prepared as follows: 0.85% saline (150 mM NaCl) was added to a one liter Pyrex® glass beaker, followed by 50 mM succinate buffer (final concentration 5 mM) and the 13vPnC, at a total volume of 500 mL. The 13vPnC formulation with 0.05% Tween™80 was prepared as follows: 0.85% saline (150 mM NaCl) was added to a one liter Pyrex® glass beaker, followed by 50 mM succinate buffer (final concentration 5 mM), 0.05% Tween™80 and the 13vPnC, at a total volume of 500 mL. The final concentration of each serotype conjugate in the 500 mL formulations was 4.4 µg/mL (except for serotype 6B, which was 8.8 µg/mL). The 500 mL formulations were homogenized via a rotor/stator homogenizer at 6,000 rpm (2-8° C.) for 120 minutes. The homogenization process created an air-liquid interface (with air bubbles).

The stability of the 13vPnC formulation with (Table 1) and without (Table 1) 0.05% Tween™80 was assessed over a two hour time period as follows: Samples (20-30 mL) were removed at zero, thirty and one hundred-twenty minutes from the 0.0% and 0.05% Tween™80 formulations, the samples were diluted 1:2 in protein diluent (Array® 360 protein diluent (Cat. No. 663630); Beckman Coulter Inc.; Fullerton, Calif.) and the antigenicity of all thirteen serotypes of the 13vPnC were assayed (see, Table 1) on an Array® 360 system.

As is shown in Table 1, there was a significant decrease in antigenicity of the thirteen serotype polysaccharides (formulated without Tween™80) within the two hour assay. Quite significantly however, the 13vPnC formulation comprising 0.05% Tween™80 (Table 1), demonstrated robust stability with no reduction in the antigenicity throughout the two hour antigenicity assay.

TABLE 1

STABILITY ASSAY OF 13VPNC FORMULATED WITH AND WITHOUT TWEEN™80

| | 13vPnC without Tween80 | | | | 13vPnC with 0.05% Tween80 | | |
| --- | --- | --- | --- | --- | --- | --- | --- |
| Serotype | Antigenicity 0 minutes | Antigenicity 30 minutes | Antigenicity 120 minutes | Serotype | Antigenicity 0 minutes | Antigenicity 30 min | Antigenicity 120 min |
| 1 | 4.8 µg/ml | 4.2 µg/ml | 2.4 µg/ml | 1 | 5.1 µg/ml | 5.0 µg/ml | 5.2 µg/ml |
| 3 | 4.8 µg/ml | 4.1 µg/ml | 1.7 µg/ml | 3 | 5.0 µg/ml | 5.0 µg/ml | 5.2 µg/ml |
| 4 | 5.8 µg/ml | 5.0 µg/ml | 3.1 µg/ml | 4 | 6.1 µg/ml | 6.1 µg/ml | 6.2 µg/ml |
| 5 | 3.4 µg/ml | 3.0 µg/ml | 2.0 µg/ml | 5 | 3.6 µg/ml | 3.6 µg/ml | 3.7 µg/ml |
| 6A | 4.9 µg/ml | 3.8 µg/ml | 1.3 µg/ml | 6A | 5.4 µg/ml | 5.4 µg/ml | 5.6 µg/ml |
| 6B | 10.0 µg/ml | 5.6 µg/ml | 1.4 µg/ml | 6B | 10.6 µg/ml | 10.6 µg/ml | 10.5 µg/ml |
| 7F | 4.7 µg/ml | 3.4 µg/ml | 1.0 µg/ml | 7F | 5.3 µg/ml | 5.2 µg/ml | 5.3 µg/ml |
| 9V | 5.6 µg/ml | 4.7 µg/ml | 2.5 µg/ml | 9V | 6.1 µg/ml | 6.1 µg/ml | 6.2 µg/ml |
| 14 | 7.6 µg/ml | 6.4 µg/ml | 3.0 µg/ml | 14 | 8.2 µg/ml | 8.3 µg/ml | 8.3 µg/ml |
| 18C | 5.6 µg/ml | 4.4 µg/ml | 1.7 µg/ml | 18C | 6.2 µg/ml | 6.1 µg/ml | 6.2 µg/ml |
| 19A | 6.4 µg/ml | 4.5 µg/ml | 1.9 µg/ml | 19A | 6.8 µg/ml | 6.8 µg/ml | 6.8 µg/ml |
| 19F | 5.4 µg/ml | 2.6 µg/ml | 0.0 µg/ml | 19F | 6.1 µg/ml | 6.2 µg/ml | 6.0 µg/ml |
| 23F | 4.5 µg/ml | 2.8 µg/ml | 0.9 µg/ml | 23F | 5.2 µg/ml | 5.2 µg/ml | 5.2 µg/ml |

The 13vPnC/Tween™80 formulation was further tested for stability against high shear forces. In this experiment, a 100 mL 13vPnC composition (4.4 µg/mL serotypes 1, 3, 4, 5, 6A, 7F, 9V, 14, 18C, 19A, 19F, 23F and 8.8 µg/mL serotype 6B, 5 mM succinate buffer, 150 mM NaCl and 0.25 mg/mL AlPO$_4$) was added to three 250 mL glass bottles comprising either 0.0%, 0.01% or 0.05% Tween™80. The three bottles were then vortexed for thirty minutes (2-8° C.) on a vortexer (Vortex-Genie® 2; Scientific Industries, Inc.; Bohemia, N.Y.) and an air-liquid interface was created at the maximum speed setting. After thirty minutes 10-30 mL samples were taken from each bottle, diluted 1:2 in Array® 360 protein diluent and the antigenicity of the thirteen serotypes assayed on an Array® 360 system.

As seen in Table 2 below, the 13vPnC formulated without Tween™80 (0.0%) had on average a 20% decrease in antigenicity after vortexing. The 13vPnC formulated with 0.01% Tween™80 had a decrease in antigenicity ranging from 2-10% (average 8%) and the 13vPnC formulated with 0.05% Tween™80 had a decrease in antigenicity ranging from 0-8% (average 3%). Thus, the data presented in Table 2 demonstrate that the 13vPnC formulated with either 0.01% or 0.05% Tween™80 were significantly stabilized against shear forces, relative to the 13vPnC formulated in the absence of Tween™80.

Example 2

Formulations Comprising Surfactant Stabilize and Prevent Aggregation of Streptococcal C5a Peptidase The streptococcal C5a peptidase (SCP) used in this example was expressed and purified as follows. The SCP was expressed recombinantly in *E. coli* using an arabinose inducible system. Standard fermentation protocols for *E. coli* using animal-free defined medium and subsequent cell lysis were followed. Recombinant SCP was purified from the soluble fraction of the cell lysate by saturation to 60% (approximately 3 M) ammonium sulfate while stirring for 12-24 hours. The saturated lysate was centrifuged, supernatant retained and loaded onto a phenyl Sepharose hydrophobic interaction column. Bound material was then eluted with 1 M ammonium sulfate, 20 mM Tris-Cl, pH 7.5, concentrated, and diafiltered against PBS, pH 7.4. The purified recombinant SCP (rSCP) was diluted to ~10 mg/mL with PBS, pH 7.4 and passed through a Posidyne filter to remove endotoxin, followed by a final filtration (0.2 mM) for sterility and stored frozen (−25° C.).

The purified SCP (55 µg/mL) was then formulated with 0.025% Tween™80 or without Tween™80 (0.0%) in the following buffers: 5 mM succinate buffer at pH 6.0, 10 mM

TABLE 2

STABILIZING EFFECT OF TWEEN™80 AGAINST SHEAR FORCES

| Serotype | Antigenicity 0.0% tw80 | Antigenicity 0.0% tw80 + vortex | Antigenicity 0.01% tw80 | Antigenicity 0.01% tw80 + vortex | Antigenicity 0.05% tw80 | Antigenicity 0.05% tw80 + vortex |
| --- | --- | --- | --- | --- | --- | --- |
| 1 | 4.7 µg/mL | 3.6 µg/mL | 4.8 µg/mL | 4.3 µg/mL | 4.7 µg/mL | 4.6 µg/mL |
| 3 | 4.6 µg/mL | 3.4 µg/mL | 4.7 µg/mL | 4.2 µg/mL | 4.7 µg/mL | 4.4 µg/mL |
| 4 | 5.5 µg/mL | 4.4 µg/mL | 5.9 µg/mL | 5.4 µg/mL | 5.9 µg/mL | 5.6 µg/mL |
| 5 | 3.2 µg/mL | 2.5 µg/mL | 3.5 µg/mL | 3.2 µg/mL | 3.3 µg/mL | 3.3 µg/mL |
| 6A | 4.3 µg/mL | 3.6 µg/mL | 4.6 µg/mL | 4.5 µg/mL | 4.7 µg/mL | 4.8 µg/mL |
| 6B | 9.7 µg/mL | 7.7 µg/mL | 10.2 µg/mL | 9.6 µg/mL | 10.2 µg/mL | 10.1 µg/mL |
| 7F | 4.6 µg/mL | 3.5 µg/mL | 5.4 µg/mL | 5.0 µg/mL | 5.4 µg/mL | 5.3 µg/mL |
| 9V | 5.3 µg/mL | 4.1 µg/mL | 5.7 µg/mL | 5.1 µg/mL | 5.6 µg/mL | 5.3 µg/mL |
| 14 | 6.8 µg/mL | 5.4 µg/mL | 7.3 µg/mL | 6.7 µg/mL | 7.4 µg/mL | 6.8 µg/mL |
| 18C | 4.1 µg/mL | 3.4 µg/mL | 4.5 µg/mL | 4.3 µg/mL | 4.5 µg/mL | 4.5 µg/mL |
| 19A | 5.1 µg/mL | 4.2 µg/mL | 5.5 µg/mL | 5.3 µg/mL | 5.6 µg/mL | 5.4 µg/mL |
| 19F | 4.8 µg/mL | 3.6 µg/mL | 5.2 µg/mL | 4.9 µg/mL | 5.2 µg/mL | 5.1 µg/mL |
| 23F | 3.0 µg/mL | 2.4 µg/mL | 3.4 µg/mL | 3.3 µg/mL | 3.5 µg/mL | 3.4 µg/mL | phosphate buffer at pH 7.0, 10 mM phosphate buffer at 7.4 or 10 mM Tris buffer at pH 7.5 and filled in separate BD Hypak SCF™ syringes. The syringes were then placed on an a horizontal orbital shaker at 2-8° C., shaken at 180 cpm for two days and the SCP protein concentration determined by the modified Lowry assay.

Figure 1B:
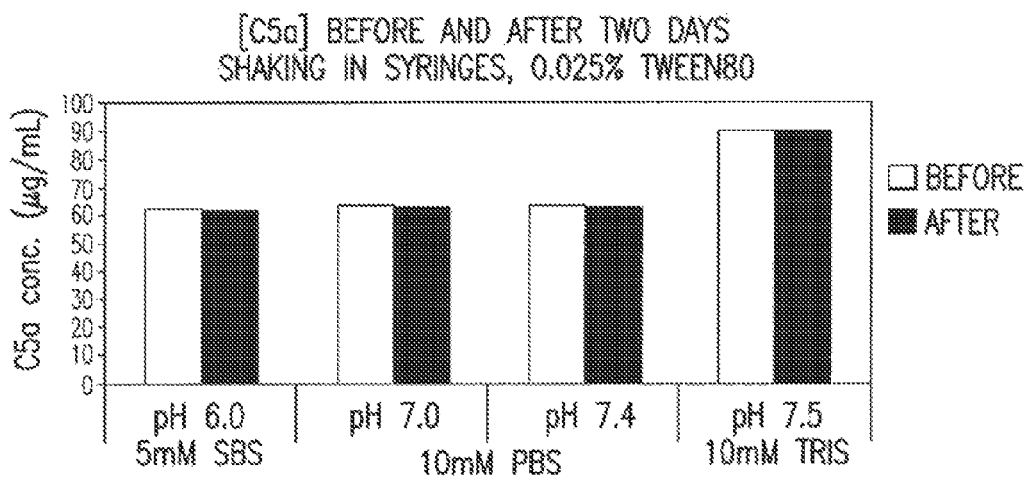

As shown in FIG. 1, the stability of SCP was greatly enhanced when formulated with Tween™80. For example, after two days on the orbital shaker, the SCP formulated without Tween™80 (FIG. 1A) demonstrated a significant decrease (e.g., greater than 90%) in the SCP concentration each of the buffers tested. However, as shown in FIG. 1B, the addition of 0.025% Tween™80 to the SCP buffer formulations, prior to being placed on the orbital shaker for two days, completely inhibited the SCP loss which was observed in FIG. 1A.

The storage stability of the SCP/Tween™80 (0.025%) formulation was also assessed at 25° C. and 37° C. for eight weeks and six weeks, respectively (data not shown). Briefly, the SCP (200 μg) was formulated in either succinate buffer or phosphate buffer as follows: succinate buffer (5 mM, pH 6.0) or phosphate buffer (15 mM, pH 7.4), 0.9% NaCl and 0.025% Tween™80. The stability of the SCP/Tween™80 formulations were assayed by size-exclusion-HPLC, modified Lowry total protein assay and visual inspection for precipitation. It was observed in this study, that the SCP/Tween™80 formulations (in either buffer) were completely stable at 25° C. and 37° C. for the entire stability study (i.e., up to eight weeks and six weeks, respectively).

Example 3

The Influence of Siliconized Container Means on the Stability of 13vPnC

Previous experiments indicated (data not shown) that 13vPnC immunogenic compositions precipitated and/or aggregated when filled in ready to use (single-dose) Becton Dickinson® (BD) Hypak Type 1 borosilicate glass syringes treated with Dow Corning® medical grade DC 360 silicone and capped with West 4432/50 latex free stoppers (chlorobutyl) and EZ tip cap West 7025/65 (Synthetic Isoprene Bromobutyl Blend; West Pharmaceutical®, Lionville, Pa.). In these experiments, the 13vPnC was formulated in 5 mM succinate buffer containing 0.85% NaCl and 4.4 μg/ml of S. pneumoniae serotypes 1, 3, 4, 5, 6A, 7F, 9V, 14, 18C, 19A, 19F and 23F and 8.8 μg/ml of S. pneumoniae serotype 6B, with and without 0.25 mg/mL aluminum phosphate as an adjuvant. It was observed that, in the absence of $AlPO_4$, the 13vPnC particulates were readily observable, whereas, in the presence of $AlPO_4$, the 13vPnC particulates were significantly diminished and more difficult to detect.

In the present example, a series of container and closure components (i.e., container means) were examined to identify what components were inducing or contributing to 13vPnC particulate formation. The container means tested comprised syringes, stoppers and vials and are listed below in Table 3. The BD and West stoppers listed in Table 3 were siliconized, using either the Huber or Jar process. The Huber process of siliconization is more controlled and yielded 30 to 60 μg/cm2 of silicone on the surface of the stopper, while the Jar process of siliconization resulted in 150 to 300 μg/cm2 of silicone on the surface of the stopper. Based on theoretical calculations, about 15% of the surface area of the stopper is exposed to the product in the syringe, suggesting that for the Huber and Jar process between 4.5 to 9 μg and 22.5 to 45 μg of silicone is extractable from the stoppers, respectively.

Materials

The silicone was Dow Corning® 360 Medical Fluid 1000 centistokes (batch No. 0001846266). The 7vPnC was formulated in 5 mM succinate buffer containing 0.85% NaCl and 4.4 μg/ml of S. pneumoniae serotypes 4, 9, 14, 18C, 19F and 23F and 8.8 μg/ml of S. pneumoniae serotype 6B, with and without 0.25 mg/ml aluminum phosphate. The 13vPnC was formulated in 5 mM succinate buffer containing 0.85% NaCl and 4.4 μg/ml of S. pneumoniae serotypes 1, 3, 4, 5, 6A, 7F, 9V, 14, 18C, 19A, 19F and 23F and 8.8 μg/ml of S. pneumoniae serotype 6B, with and without 0.25 mg/ml aluminum phosphate. Monovalent S. pneumoniae serotype 6B was formulated (5 mM succinate buffer containing 0.85% NaCl, without aluminum phosphate) at a concentration of 61 μg/ml to simulate the total saccharide concentration of the 13vPnC formulations.

Methods

The 7vPnC and 13vPnC were formulated as described above, and 35 ml of a given formulation was added to a clear 250 ml Nalgene® bottle. Into each Nalgene® bottle, the container means components listed in Table 3 were added. The Nalgene® bottles were then placed on a Labline® Orbit Shaker and swirled overnight at 50 rpm. The results are summarized in Table 3.

Visual Appearance. The Nalgene® bottles containing each of the container means components were held up to a fluorescence light in the laboratory. A path of a beam of light (Tindel effect) passing through the samples allowed for the detection of particulates.

Protein Assay. The total protein and protein bound to aluminum was determined by measuring the total protein concentration in the formulated immunogenic composition and the protein associated with the aluminum pellet, respectively (an aliquot of the immunogenic composition was centrifuged and the pellet was re-suspended in saline). Assays were performed using the Pierce Modified Lowry protein assay (catalog #23240) with bovine serum albumin as a standard.

Results

In the first series of experiments, the 13vPnC immunogenic compositions were formulated without $AlPO_4$ and exposed to a series of container means listed below in Table 3. It was clearly evident from the data (Table 3), that the container means components that were treated with silicone oil induced the formation of white particles. In contrast, no particulates were detected in the presence of the non-siliconized Daikyo® stoppers (Daikyo Seiko, Ltd., Japan) and Schott vials (Schott North America Inc.; Lebanon, Pa.).

TABLE 3

EFFECT OF DIFFERENT CONTAINER MEANS COMPONENTS ON 13VPNC, FORMULATED WITHOUT $ALPO_4$

| Container Means Components | Number of Container Means Components Added | Appearance (Visual Inspection) |
| --- | --- | --- |
| Control-13vPnC without AlPO4 | None | No Particulate |
| BD Hypak BSCF 1-3 ml 4432/50 Grey Si WWD Stoppers | 10 | Particulates |
| BD Hypak BSCF 1-3 ml 4432/50 Grey Si Huber Processed Stoppers | 10 | Particulates |
| West 890 Ready to Sterilize Stoppers | 10 | Particulates |
| BD Hypak BSCF 1-3 ml W4416/50 Grey Si 1000 WWD Stoppers | 10 | Particulates |
| Helvoet 6213 Stoppers | 10 | Particulates |
| Daikyo Vial Stoppers (D777-1 B2-40 F451 plug stoppers) | 10 | No Particulate |

TABLE 3-continued

EFFECT OF DIFFERENT CONTAINER MEANS COMPONENTS
ON 13VPNC, FORMULATED WITHOUT ALPO$_4$

| Container Means Components | Number of Container Means Components Added | Appearance (Visual Inspection) |
|---|---|---|
| BD Hypak BSCF 1-3 ml LLA EZGTC W7025/65 Syringe Barrels | 4 | Particulates |
| Hypak NSCF 1-3 ml 4023/50 B2-40 Daikyo Stoppers | 10 | No Particulate |
| Syringe E-Z Grip Tip Cap W7025/65 EZ IITC | 10 | No Particulate |
| 2 ml, 13 mm Schott Type 1 glass vials | 4 | No Particulate |
| Silicone Oil (Dow Chemical Medical grade 360) | 500 µL (1.43%) | Particulates |
| Schott TopPac Syringes | 4 | No Particulate |

The monovalent *S. pneumoniae* serotype 6B was chosen as a model for the 13vPnC and was formulated at 61.6 µg/ml (without AlPO$_4$) to simulate the total saccharide concentration in the 13vPnC formulation. Silicone (Dow Corning 360 Medical Fluid) was added to aliquots of the formulated monovalent 6B, ranging from 2 ppm to 100 ppm. The mixtures were placed on a Labline® Orbit Shaker for 2 hours at 50 rpm. As indicated below in Table 4, fiber-like white particulates were observed at all silicone (Si) concentrations.

TABLE 4

EFFECT OF SILICONE CONCENTRATION
ON THE FORMATION OF PARTICULATES

| Silicone Concentration | Appearance (Visual Inspection) |
|---|---|
| 2 ppm (1 µl of Si to 500 mL Formulation) | Fiber-like white particulates |
| 5 ppm (2.5 µl of Si to 500 mL Formulation) | Fiber-like white particulates |
| 10 ppm (5 µl of Si to 500 mL Formulation) | Fiber-like white particulates |
| 15 ppm (7.5 µl of Si to 500 mL Formulation) | Fiber-like white particulates |
| 20 ppm (10 µl of Si to 500 mL Formulation) | Fiber-like white particulates |
| 100 ppm (2 µl of Si to 20 mL Formulation) | Fiber-like white particulates |

The amount of silicone in 13vPnC formulations (without AlPO$_4$) was also examined. The silicone concentration was determined by DC Plasma Emission Spectroscopy (data not shown). In this method, the content of 25 syringes were pooled and extracted with two 50 ml portions of cyclohexane/isopropyl alcohol mixture. The extracts were combined and evaporated. The residual was solubilized and tested as per existing methods for silicone determination on rubber stoppers. The results indicated that between 15.8 to 19.0 µg of silicone is extractable from each syringe. This amount corresponds to 2.7% to 3.3% of silicone.

In a separate series of experiments, in which the 13vPnC was formulated in the presence of AlPO$_4$ and subjected to the same container means set forth in Table 3, it was elucidated that the silicone and the "free" protein (13vPnC) in solution was responsible for the formation of the particulates (data not shown). FTIR analysis of the particulates also indicated that the particulate consisted of protein and silicone (data not shown). It was determined in these experiments, that about 85% of the 13vPnC is bound to the AlPO$_4$, wherein the remaining 15% was free (not bound to AlPO$_4$) 13vPnC in solution. In contrast, it was observed that 7vPnC formulated with AlPO$_4$ was 100% bound to the AlPO$_4$ (data not shown).

To elucidate the effect of free protein-polysaccharide on the formation of particulates, 25 ml of both 7vPnC and 13vPnC were aliquoted and transferred to a 50 ml centrifuge tube. The samples were centrifuged for 10 minutes at 3,000 rpm and the supernatant was carefully extracted and transferred to a Nalgene® bottle. Ten siliconized stoppers (4432 Stoppers) were added to each bottle and placed on orbital shaker at 50 rpm. After careful visual inspection, it was observed that the 7vPnC supernatant exhibited no particulate formation, thereby remaining clear and colorless. However, the 13vPnC supernatant began to show low levels of particulate in the fourth hour of observation (data not shown). This result suggested that the free protein-polysaccharide in solution, in conjunction with silicone, is responsible for the formation of the particulates.

To further elucidate the contribution of the free protein-polysaccharide in solution to the formation of particulates, monovalent *S. pneumoniae* serotypes 4 and 6B were chosen for their high and low binding to aluminum, respectively. These two monovalents were formulated at protein concentration ranging from 25 µg/ml to 200 µg/ml in the absence and presence of AlPO$_4$. Ten siliconized stoppers (4432 stoppers) were placed in each formulation, which were then placed on the orbit shaker at 50 rpm. As indicated below in Table 5, fiber-like white particulates were observed for both monovalent serotypes at all protein concentrations in the absence of AlPO$_4$. However, in the presence of AlPO$_4$, particulates were detected at lower concentrations for serotype 4 (100 µg/ml) versus serotype 6B (200 µg/ml), data not shown.

TABLE 5

EFFECT OF PROTEIN CONCENTRATION
ON THE FORMATION OF PARTICULATES

| | Appearance (Visual Inspection) | |
|---|---|---|
| | Without AlPO$_4$ | With AlPO$_4$ |
| 25 µg/mL of 6B | Fiber-like white particulates | No particulates |
| 50 µg/mL of 6B | Fiber-like white particulates | No particulates |
| 75 µg/mL of 6B | Fiber-like white particulates | No particulates |
| 100 µg/mL of 6B | Fiber-like white particulates | No particulates |
| 200 µg/mL of 6B | Fiber-like white particulates | Fiber-like white particulates |
| 25 µg/mL of Type 4 | Fiber-like white particulates | No particulates |
| 50 µg/mL of Type 4 | Fiber-like white particulates | No particulates |
| 75 µg/mL of Type 4 | Fiber-like white particulates | No particulates |
| 100 µg/mL of Type 4 | Fiber-like white particulates | Fiber-like white particulates |
| 200 µg/mL of Type 4 | Fiber-like white particulates | Fiber-like white particulates |

Example 4

Aluminum Adjuvants Inhibit the Formation of 13vPnC Particulates in the Presence of Siliconized Container Means As set forth above in Example 3, a 13vPnC immunogenic composition is a liquid formulation comprising 4.4 µg/mL of *S. pneumoniae* serotypes 1, 3, 4, 5, 6A, 7F, 9V, 14, 18C, 19A, 19F, 23F and 8.8 μg/mL of type 6B in 5 mM succinate buffer (pH 5.8) and 0.85% NaCl, which may also be formulated with or without an adjuvant (e.g., an aluminum adjuvant). The 13vPnC may also be formulated with or without an adjuvant, such as 0.25 mg aluminum/ml aluminum phosphate (AlPO$_4$). It was observed in Example 3, that 13vPnC formulated without AlPO$_4$ and filled in BD Hypak SCF™ syringes (capped with Hypak plungers) failed visual inspection due to the observation of particulates, wherein further studies revealed that the particulates were in part a result of protein-polysaccharide interactions with silicone. In the following example, syringes (and plungers) from various vendors were evaluated with 13vPnC formulations, wherein shipping and handling conditions were simulated via agitation (described below).

Materials

The 13vPnC was formulated in 5 mM succinate buffer containing 0.85% NaCl and 4.4 μg/ml of S. pneumoniae serotypes 1, 3, 4, 5, 6A, 7F, 9V, 14, 18C, 19A, 19F and 23F and 8.8 μg/ml of S. pneumoniae serotype 6B, with and without 0.25 mg/ml aluminum phosphate. The container means tested are listed below in Table 6.

TABLE 6

CONTAINER MEANS

| | Container Means | Description |
|---|---|---|
| 1 | Vetter syringes<br>Type 1 untreated glass | 1 ml long bulk format |
| 2 | Schott TopPac ® syringes | Plastic syringes |
| 3 | BD Baked syringes<br>Type 1 untreated glass | 0.1 mg silicone/barrel |
| 4 | BD Baked syringes<br>Type 1 untreated glass | 0.04 mg silicone/barrel |
| 5 | BD High viscosity syringes<br>Type 1 untreated glass | 2.25 ml syringes<br>12500 cst silicone |
| 6 | BD High viscosity syringes<br>Type 1 untreated glass | 1.0 ml syringes<br>12500 cst silicone |
| 7 | BünderGlas syringes, PS2<br>Type 1 untreated glass | 0.056 mg silicone/barrel |
| 8 | BünderGlas syringes, PS4<br>Type 1 untreated glass | 0.14 mg silicone/barrel |
| 1 | West 4023/50 Flurotec ® B2-40 plungers | Flurotec ® plungers |
| 2 | West 4023/50 Flurotec ® B2-40 plungers | Flurotec ® plungers |
| 1 | 13vPnC with AlPO$_4$ in BD Hypak syringes with West 4432 ready to use plungers and 7025/65 EZ tip caps | Positive control, high silicone |
| 2 | 13vPnC with AlPO$_4$ in un-siliconized syringes with West 4023/50 Flurotec ® B2-40 plungers | Negative control, not treated with silicone |

Methods

Formulation and Fill Procedure. Listed below in Table 7 is the recipe for a 2 liter 13vPnC formulation. Briefly, the 0.85% saline was first added to a glass beaker, followed by the 5 mM succinate buffer (pH 5.8), and then sequentially each of the S. pneumoniae serotype conjugates. The formulation was then gently mixed on a stirrer plate and filtered through a 0.22 μm Millipore® filter unit. For formulation comprising AlPO$_4$, the AlPO$_4$ (0.25 mg/ml final concentration) was then added and the formulation gently mixed. The test syringes were then filled (0.58 ml/syringe) and capped with plungers.

Shipping Simulation via Agitation. A VWR® signature Digital Multitube vortexer (Catalog No. 14005-826) was used to agitate the samples. The syringes filled with 13vPnC were placed horizontal and fixed by the two support plates of the vortexer. Samples were held at horizontal position and agitated at 500 rpm pause mode at 2-8° C. for twenty-four hours.

Nephelometry. Serotype specific antigenicities were determined by a rate nephelometry assay using type-specific antibodies. For 13vPnC with AlPO$_4$, the aluminum phosphate was solubilized by adding 1N NaOH. The solution was immediately neutralized by adding 1M citric acid. For 13vPnC without AlPO4, no solubilization and neutralization procedures were performed. The assay measures the rate of change of light scattering intensity derived from the antibody-antigen complex formed in the sample using Beckman Array 360 nephelometer.

TABLE 7

13VPNC FORMULATION TABLE

| Component | Batch Size (L) | Bulk Conc (mg/mL) | Required Conc (ug/mL) | 13vPnC with AlPO$_4$ Volume (mL) | 13vPnC without AlPO$_4$ Volume (mL) |
|---|---|---|---|---|---|
| serotype 1 | 2.000 | 0.506 | 4.4 | 17.39 | 17.39 |
| serotype 3 | 2.000 | 0.256 | 4.4 | 34.38 | 34.38 |
| serotype 4 | 2.000 | 0.530 | 4.4 | 16.60 | 16.60 |
| serotype 5 | 2.000 | 0.515 | 4.4 | 17.09 | 17.09 |
| serotype 6A | 2.000 | 0.519 | 4.4 | 16.96 | 16.96 |
| serotype 6B | 2.000 | 0.489 | 8.8 | 35.99 | 35.99 |
| serotype 7F | 2.000 | 0.500 | 4.4 | 17.60 | 17.60 |
| serotype 9V | 2.000 | 0.521 | 4.4 | 16.89 | 16.89 |
| serotype 14 | 2.000 | 0.518 | 4.4 | 16.99 | 16.99 |
| serotype 18C | 2.000 | 0.509 | 4.4 | 17.29 | 17.29 |
| serotype 19A | 2.000 | 0.511 | 4.4 | 17.22 | 17.22 |
| serotype 19F | 2.000 | 0.520 | 4.4 | 16.92 | 16.92 |
| serotype 23F | 2.000 | 0.511 | 4.4 | 17.22 | 17.22 |
| Succinate Buffer in 0.85% Saline, pH 5.8 | 2.000 | 50.0 | 5000 | 200.0 | 200.0 |
| AlPO$_4$ | 2.000 | 3.250 | 250 | 153.85 | NA |
| Saline | 2.000 | NA | NA | 1387.62 | 1541.46 |

Results

In this study, syringes from different venders, having different silicone levels (Table 6), were subject to controlled agitation conditions. The total antigenicity of each serotype was measured by Nephelometry assay for both pre-agitation and post-agitation samples. Antigenicity loss following agitation (percentage) was calculated and is shown in FIG. 2 through FIG. 7.

Figure 2:
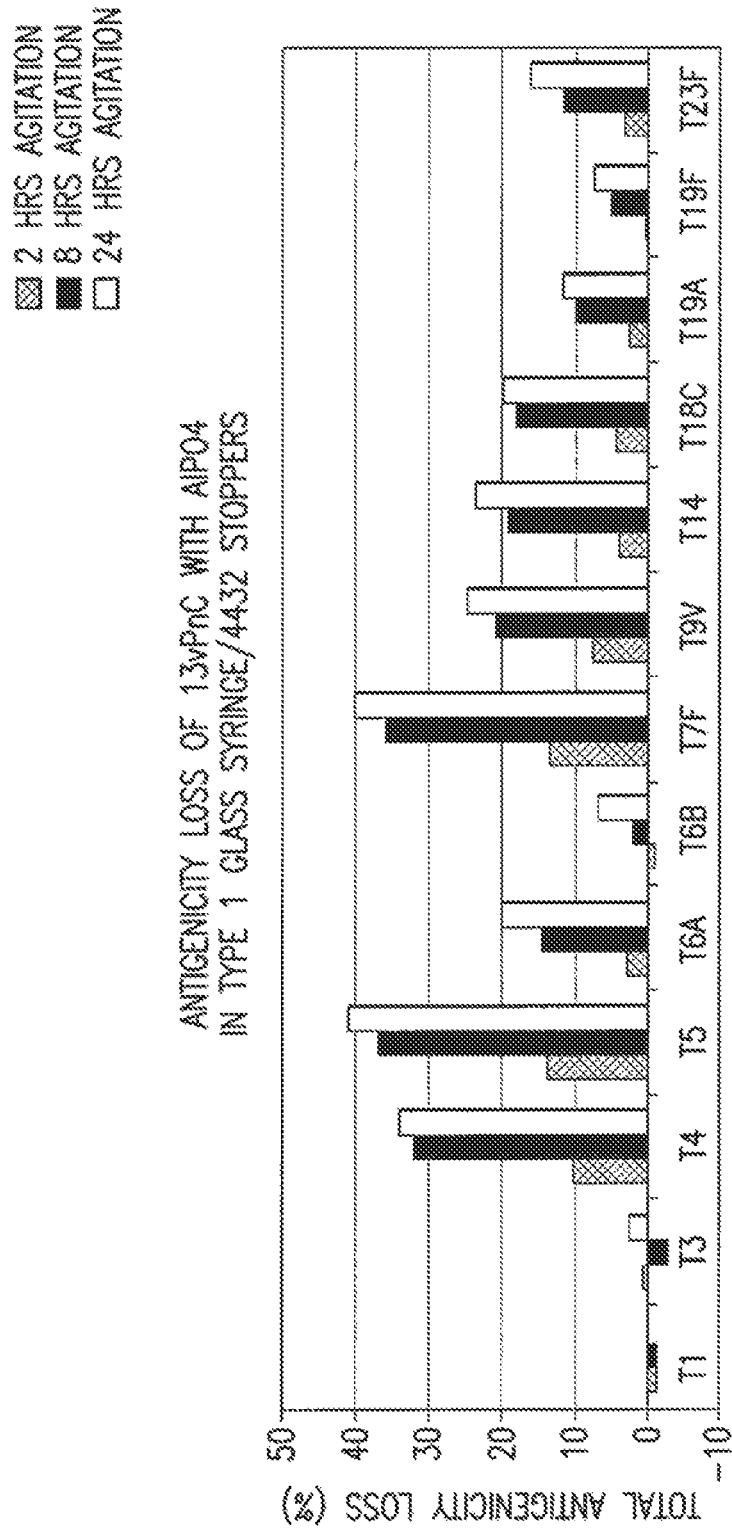
FIG. 2 shows the total antigenicity loss of the 13vPnC formulated with $AlPO_4$ (0.25 mg/ml) and filled in a BD Hypak syringe, after two hours, eight hours and twenty-four hours of agitation at 500 rpm and 2-8° C.
Figure 3:
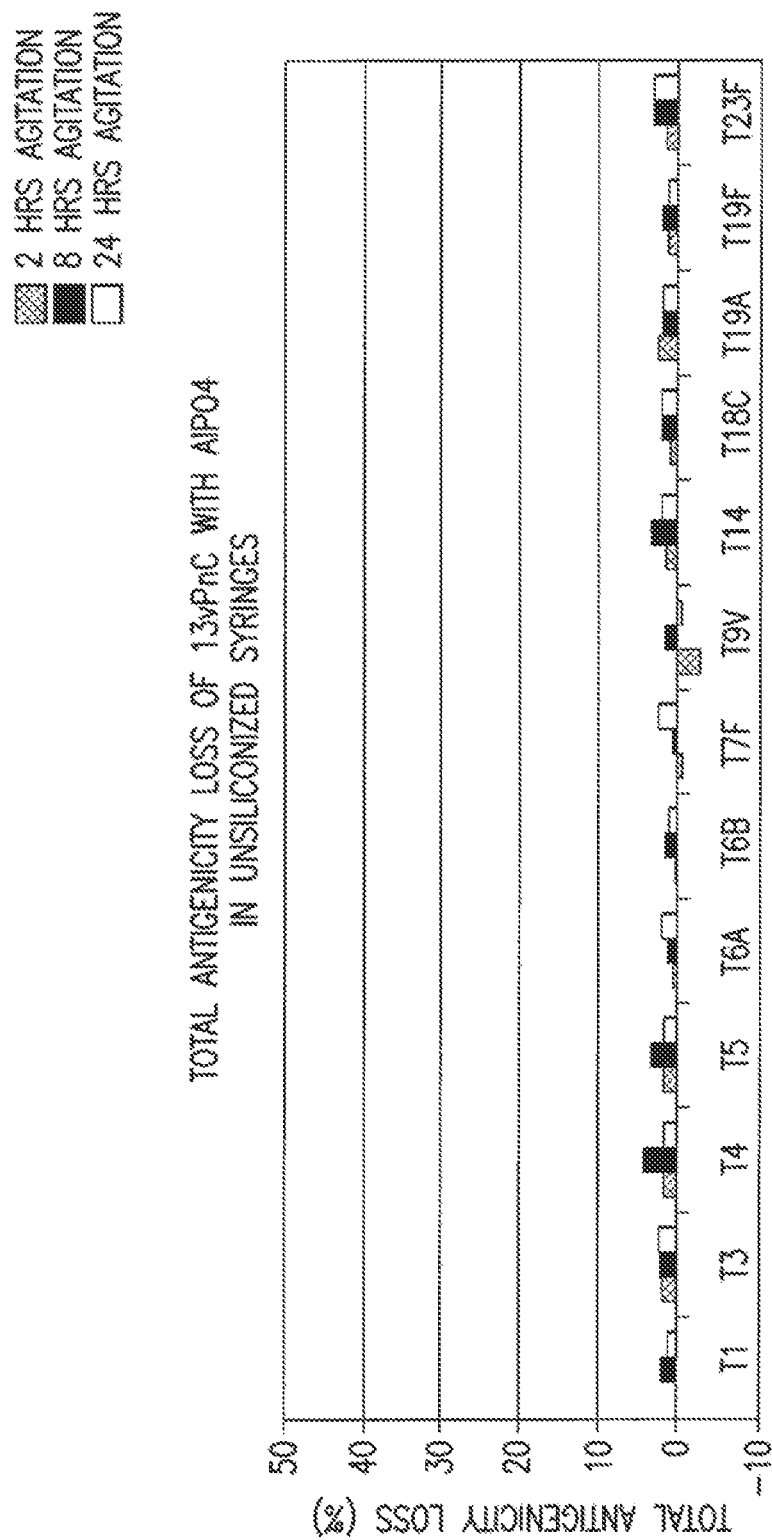
FIG. 3 shows the total antigenicity loss of the 13vPnC formulated with $AlPO_4$ (0.25 mg/ml) and filled in an unsiliconized syringe, after two hours, eight hours and twenty-four hours of agitation at 500 rpm and 2-8° C.
Figure 4:
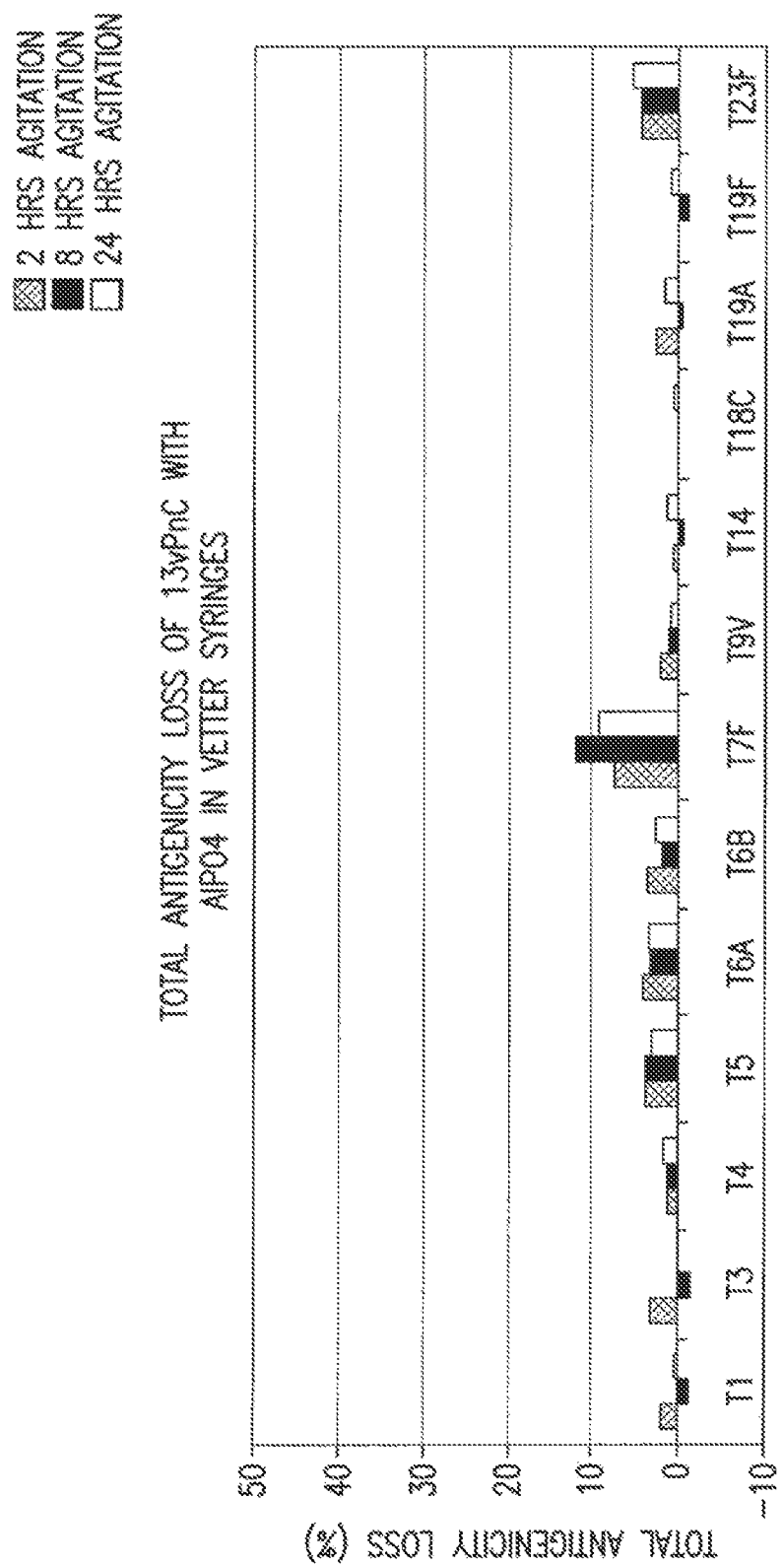
FIG. 4 shows the total antigenicity loss of the 13vPnC formulated with $AlPO_4$ (0.25 mg/ml) and filled in a Vetter syringe, after two hours, eight hours and twenty-four hours of agitation at 500 rpm and 2-8° C.
Figure 5:
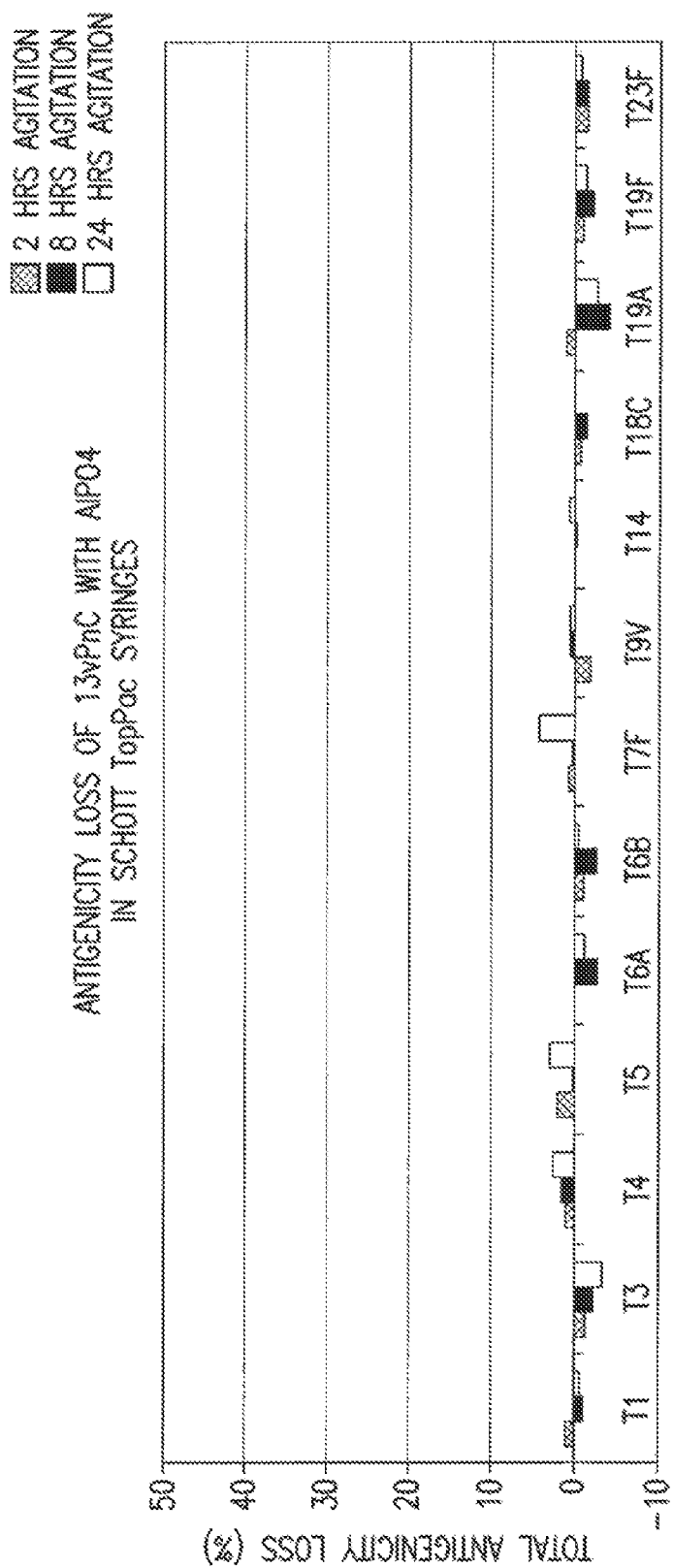
FIG. 5 shows the total antigenicity loss of the 13vPnC formulated with $AlPO_4$ (0.25 mg/ml) and filled in a Schott TopPac syringe, after two hours, eight hours and twenty-four hours of agitation at 500 rpm and 2-8° C.

Prior to the study, the agitation conditions were optimized based on the antigenicity loss of the two controls: (1) the worst-case control (positive control, high silicone; FIG. 2) and (2) the best-case control (negative control, no silicone; FIG. 3). The conditions were then optimized such that the antigenicity loss was low in positive control, yet detectable in the negative control. This was to ensure that the agitation was neither too weak to produce precipitation in the syringes; nor too strong, such that the precipitation might be caused by factors other than the silicone interaction (e.g., by shear forces). Thus, agitation at 500 rpm (pause mode) for twenty-four hours was chosen as the most suitable agitation condition, while a temperature of 2-8° C. and a horizontal position were used to simulate the conditions in real time product shipping and handling.

The results of the study are summarized as follows: The largest antigenicity losses of the 13vPnC formulated with AlPO$_4$ occurred in the syringes with higher silicone levels (data not shown). For example, of the syringes listed in Table 6, the BD Hypak syringe (control 1), the BD baked syringe (syringe 3; 0.1 mg silicone), the BD high viscosity (syringe 5) and the BünderGlas PS4 syringe (syringe 8, 0.14 mg silicone), each had one or more of the 13vPnC serotypes with greater than 10% antigenicity loss. The smallest antigenicity losses of the 13vPnC formulated with AlPO$_4$ occurred in the syringes with lower silicone levels. For example, the Vetter syringes (FIG. 4) and the Schott TopPac plastic syringes (FIG. 5) were most similar to un-siliconized syringes (FIG. 2), both demonstrating minor antigenicity losses for 13vPnC formulated with AlPO$_4$.

The influence of the aluminum phosphate on stabilizing the 13vPnC and inhibiting particulate formation in the presence of siliconized syringes was analyzed in experiments using 13vPnC formulated with and without 0.25 mg/ml AlPO$_4$, wherein syringes used were the BD baked low silicone syringes (syringe 4 in Table 6) and the BünderGlas low silicone PS2 syringes (syringe 7 in Table 6). The BD baked low silicone syringes (0.04 mg silicone/barrel) typically had less than 10% antigenicity loss for the 13vPnC serotypes formulated with AlPO$_4$ (FIG. 6A), whereas the antigenicity loss for the 13vPnC serotypes formulated without AlPO$_4$ (FIG. 6B) had antigenicity losses ranging from 5% (serotype 1) up to about 50% (serotype 23F). The BunderGlas low silicone PS2 (0.056 mg silicone/barrel) syringes had less than 5-8% antigenicity loss (depending on serotype) for 13vPnC formulated with AlPO$_4$ (FIG. 7A), whereas the antigenicity loss for the 13vPnC serotypes formulated without AlPO$_4$ (FIG. 7B) had antigenicity losses ranging from about 5% to about 30% (depending on serotype).

Thus, these data taken together indicate that: (1) the antigenicity loss of 13vPnC was greater in the syringes with higher silicone levels and (2) the 13vPnC formulated without AlPO$_4$ sustained greater antigenicity losses than 13vPnC with AlPO$_4$ in all of the syringes tested.

Example 5

Formulations Comprising Surfactant Optimize the Binding of Meningococcal Antigenic Proteins to Aluminum Salt Adjuvants The recombinant lipidated *N. meningitidis* 2086 protein (rLP2086) used in this example was expressed and purified as follows. The rLP2086 was expressed recombinantly in *E. coli* utilizing a native leader sequence. Standard fermentation protocols for *E. coli* using animal-free defined medium and subsequent cell lysis were followed. Recombinant lipidated *N. meningitidis* 2086 protein was purified from the membrane pellet with 50 mM Tris-HCl/5 mM EDTA/1% sarcosyl pH 8. This sarcosyl extract was adjusted to 1% Zwittergent 3-14 (Z3-14) and dialyzed twice against a 30 fold excess of 50 mM Tris-HCl/5 mM EDTA/1% Z3-14. The dialyzed rLP2086 extract was precipitated with 90% ethanol to remove remaining sarcosyl, and solubilized with 50 mM Tris-HCl/5 mM EDTA/1% Z3-14 pH 8. Insoluble material was removed by centrifugation, the supernatant was passed over an anion exchange chromatography column, and rLP2086 was collected in the unbound fraction. The unbound material was then dialyzed twice against a 30-fold excess of 25 mM NaAc/1% Z3-14 pH 4.5, and passed over a cation exchange chromatography column. The rLP2086 was eluted with a 0-0.3M NaCl gradient and stored frozen (−25° C.).

The purified rLP2086 was then formulated with 150 mM NaCl, 0.020% Tween™80, 0.25 mg Al/mL of AlPO$_4$, and in the following buffers: 10 mM phosphate buffer at pH 7.0 and 5 mM succinate buffer at pH 6.0. Table 8 compares protein binding percentage to the AlPO$_4$ adjuvant.

TABLE 8

RLP2086 BINDING TO ADJUVANT

| Buffer | Total Protein Conc. (µg/mL) | AlPO$_4$ Bound Protein (%) |
|---|---|---|
| 10 mM Phosphate buffer pH 7.0 containing 150 mM NaCl, 0.02% polysorbate 80 and 0.25 mg Al/mL of AlPO$_4$ | 400 | 68 |
|  | 120 | 82 |
| 5 mM Succinate buffer pH 6.0 containing 150 mM NaCl, 0.02% polysorbate 80 and 0.25 mg Al/mL of AlPO$_4$ | 400 | 81 |
|  | 120 | 100 |

REFERENCES

Baldwin, "Contamination of insulin by silicone oil: A potential hazard of plastic insulin syringes", *Diabet. Med.*, 5:789-790, 1988.

Bartzoka, Brook and McDormott, "Protein-Silicone Interactions at Liquid-Liquid Interfaces. In K. L. Mittal and P. Kumar (eds.), *Emulsions, Foams and Thin Films*, Dekker, New York, pp. 371-380, 2000.

Bartzoka, Brook and McDormott, "Protein-Silicone Films: Establishing the Strength of the Protein-Silicone Interaction", *Langmuir* 14:1892-1898, 1998[b].

Bartzoka, Brook and McDormott, "Protein-Silicone Interactions: How Compatible Are the Two Species?", *Langmuir* 14:1887-1891, 1998[a].

Bartzoka, Chan and Brook, "Protein-Silicone Synergism at Liquid/Liquid Interfaces", *Langmuir* 16:4589-4593, 2000.

Bernstein, "Clouding and Deactivation of Clear (Regular) Human Insulin: Association with Silicone Oil from Disposable Syringes", *Diabetes Care* 10:786-787, 1987.

Bernstein, "Clouding and deactivation of clear (regular) human insulin: Association with silicone oil from disposable syringes?", *Diabetes Care*, 10:786-787, 1987.

Bolgiano et al., "Effect of Physico-Chemical Modification on the Immunogenicity of *Haemophilus influenzae* Type b Oligosaccharide-CRM$_{197}$ Conjugate Vaccines", *Vaccine*, 19:3189-3200, 2001.

Chantelau and Berger, "Pollution of insulin with silicone oil, a hazard of disposable plastic syringes", *Lancet*, 1:1459, 1985.

Chantelau et al., "Silicone oil released from disposable insulin syringes", *Diabetes care*, 9:672-673, 1986.

Chantelau, "Silicone oil contamination of insulin", *Diabet. Med.*, 6:278, 1989.

Chantelau, Burger and Bohlken, "Silicone Oil Released from Disposable Insulin Syringes", *Diabetes Care* 9: 672-673, 1986.

Collier and Dawson, "Insulin syringes and silicone oil", *Lancet*, 5:789-790, 1985.

Ho et al., "Physico-Chemical and Immunological Examination of the Thermal Stability of Tetanus Toxoid Conjugate Vaccines", *Vaccine*, 20:3509-3522, 2002.

Ho et al., "Solution Stability of the Subunit Components of Meningococcal C Oligosaccharide-CRM$_{197}$ Conjugate Vaccines", *Biotech. Appl. Biochem.*, 33:91-98, 2001.

Jones et al., "Silicone Oil Induced Aggregation of Proteins", *J. Pharmaceutical Sci.*, 94(4):918-927, 2005.

Kajihara et al., "Development of new drug delivery system for protein drugs using silicone", *J. Control. Rel.* 66:49-61, 2000.

Polin, "The Ins and Outs of Prefilled Syringes," *Pharmaceutical and Medical Packaging News Article Index*, May 2003.

Sun et al., "Protein Denaturation Induced by Cyclic Silicone", *Biomaterials* 18:1593-1597, 1998.

What is claimed is:

1. A formulation comprising (i) a pH buffered saline solution, wherein the buffer has a pKa of about 3.5 to about 7.5, (ii) an aluminum salt and (iii) one or more polysaccharide-protein conjugates, wherein the formulation is comprised in a siliconized container means and inhibits aggregation induced by the siliconized container means.

2. The formulation of claim 1, wherein the formulation further comprises polysorbate 80, and wherein the final concentration of the polysorbate 80 in the formulation is at least 0.001% to 10% polysorbate 80 weight/volume of the formulation.

3. The formulation of claim 1, wherein the polysaccharide-protein conjugate comprises one or more pneumococcal polysaccharides.

4. The formulation of claim 1, wherein the formulation further comprises one or more meningococcal polysaccharides, one or more meningococcal antigenic proteins, or a combination thereof.

5. The formulation of claim 1, wherein the formulation further comprises one or more streptococcal polysaccharides, one or more streptococcal antigenic proteins, or a combination thereof.

6. The formulation of claim 1, wherein the formulation further comprises an adjuvant.

7. The formulation of claim 1, wherein the pH buffered saline solution has a pH of 5.5 to 7.5.

8. The formulation claim 1, wherein the buffer is phosphate, succinate, histidine or citrate.

9. The formulation of claim 1, wherein the salt in the pH buffered saline solution comprises magnesium chloride, potassium chloride, sodium chloride or a combination thereof.

10. The formulation of claim 1, wherein the aluminum salt is aluminum hydroxide, aluminum phosphate or aluminum sulfate.

11. The formulation of claim 10, wherein the aluminum salt is aluminum phosphate.

12. The formulation of claim 1, wherein the buffer is histidine, the salt in the pH buffered saline solution is sodium chloride and the aluminum salt is aluminum phosphate.

13. The formulation of claim 1, wherein the buffer is histidine at pH 5.8, the salt in the pH buffered saline solution is sodium chloride and the aluminum salt is aluminum phosphate.

14. The formulation claim 1, wherein the formulation further comprises a surfactant selected from the group consisting of polysorbate 20, polysorbate 40, polysorbate 60, polysorbate 65, polysorbate 80, polysorbate 85, nonylphenoxypolyethoxethanol, octylphenoxypolyethoxethanol, oxtoxynol 40, nonoxynol-9, triethanolamine, triethanolamine polypeptide oleate, polyoxyethylene-660 hydroxystearate, polyoxyethylene-35ricinoleate, soy lecithin and a poloxamer.

15. The formulation of claim 1, wherein the one or more polysaccharide-protein conjugate comprises one or more pneumococcal polysaccharides, the buffer is histidine, the salt in the pH buffered saline solution is sodium chloride and the aluminum salt is aluminum phosphate.

16. The formulation of claim 1, wherein the one or more polysaccharide-protein conjugate comprises one or more pneumococcal polysaccharides, the buffer is histidine at pH 5.8, the salt in the pH buffered saline solution is sodium chloride and the aluminum salt is aluminum phosphate.

17. The formulation of claim 1, wherein the one or more polysaccharide-protein conjugate comprises an *S. pneumoniae* serotype 4 polysaccharide conjugated to a CRM197 polypeptide, an *S. pneumoniae* serotype 6B polysaccharide conjugated to a CRM197 polypeptide, an *S. pneumoniae* serotype 9V polysaccharide conjugated to a CRM197 polypeptide, an *S. pneumoniae* serotype 14 polysaccharide conjugated to a CRM197 polypeptide, an *S. pneumoniae* serotype 18C polysaccharide conjugated to a CRM197 polypeptide, an *S. pneumoniae* serotype 19F polysaccharide conjugated to a CRM197 polypeptide, and an *S. pneumoniae* serotype 23F polysaccharide conjugated to a CRM197.

18. The formulation of claim 1, wherein the one or more polysaccharide-protein conjugate comprises an *S. pneumoniae* serotype 4 polysaccharide conjugated to a CRM197 polypeptide, an *S. pneumoniae* serotype 6B polysaccharide conjugated to a CRM197 polypeptide, an *S. pneumoniae* serotype 9V polysaccharide conjugated to a CRM197 polypeptide, an *S. pneumoniae* serotype 14 polysaccharide conjugated to a CRM197 polypeptide, an *S. pneumoniae* serotype 18C polysaccharide conjugated to a CRM197 polypeptide, an *S. pneumoniae* serotype 19F polysaccharide conjugated to a CRM197 polypeptide, an *S. pneumoniae* serotype 23F polysaccharide conjugated to a CRM197 polypeptide, an *S. pneumoniae* serotype 1 polysaccharide conjugated to a CRM197 polypeptide, an *S. pneumoniae* serotype 3 polysaccharide conjugated to a CRM197 polypeptide, an *S. pneumoniae* serotype 5 polysaccharide conjugated to a CRM197 polypeptide, an *S. pneumoniae* serotype 6A polysaccharide conjugated to a CRM197 polypeptide, an *S. pneumoniae* serotype 7F polysaccharide conjugated to a CRM197 polypeptide and an *S. pneumoniae* serotype 19A polysaccharide conjugated to a CRM197 polypeptide.

19. The formulation of claim 1, wherein the siliconized container means is selected from the group consisting of a vial, a syringe, a flask, a fermentor, a bioreactor, tubing, a pipe, a bag, a jar, an ampoule, a cartridge and a disposable pen.

20. The formulation of claim 19, wherein siliconized container means is a syringe.

21. The formulation of claim 8, wherein the buffer is succinate at a final concentration of 1 mM to 10 mM and pH 5.8 to 6.0.

22. The formulation of claim 21, wherein the succinate buffer is at a final concentration of 5 mM.

* * * * *

(12) INTER PARTES REVIEW CERTIFICATE (1142nd)
United States Patent
Khandke et al.

(10) Number: US 8,562,999 K1
(45) Certificate Issued: Apr. 1, 2019

(54) FORMULATIONS WHICH STABILIZE AND INHIBIT PRECIPITATION 0F IMMUNOGENIC COMPOSITIONS

(71) Applicants: Lakshmi Khandke; Ronald Malone; Cindy Xudong Yang; Hanyoung Han; Jee Loon Look; Zhaowei Jin; Robert C. Seid, Sr.; Ying Chen

(72) Inventors: Lakshmi Khandke; Ronald Malone; Cindy Xudong Yang; Hanyoung Han; Jee Loon Look; Zhaowei Jin; Robert C. Seid, Sr.; Ying Chen

(73) Assignee: Wyeth LLC

Trial Number:

IPR2017-00390 filed Dec. 2, 2016

Inter Partes Review Certificate for:

Patent No.: 8,562,999
Issued: Oct. 22, 2013
Appl. No.: 13/631,573
Filed: Sep. 28, 2012

The results of IPR2017-00390 are reflected in this inter partes review certificate under 35 U.S.C. 318(b).

INTER PARTES REVIEW CERTIFICATE
U.S. Patent 8,562,999 K1
Trial No. IPR2017-00390
Certificate Issued Apr. 1, 2019

AS A RESULT OF THE INTER PARTES REVIEW PROCEEDING, IT HAS BEEN DETERMINED THAT:

Claims 7-9, 12, 13, 15, 16, 21 and 22 are cancelled.

\* \* \* \* \*

(12) INTER PARTES REVIEW CERTIFICATE (2473rd)
United States Patent (10) Number: US 8,562,999 K2
Khandke et al. (45) Certificate Issued: Oct. 25, 2021

(54) FORMULATIONS WHICH STABILIZE AND INHIBIT PRECIPITATION OF IMMUNOGENIC COMPOSITIONS

(71) Applicant: Wyeth LLC

(72) Inventors: Lakshmi Khandke; Ronald Malone; Cindy Xudong Yang; Hanyoung Han; Jee Loon Look; Zhaowei Jin; Robert C. Seid, Jr.; Ying Chen

(73) Assignee: Wyeth LLC

Trial Numbers:

IPR2017-00378 filed Dec. 1, 2016
IPR2017-00380 filed Dec. 1, 2016

Inter Partes Review Certificate for:

Patent No.: 8,562,999
Issued: Oct. 22, 2013
Appl. No.: 13/631,573
Filed: Sep. 28, 2012

The results of IPR2017-00378 and IPR2017-00380 are reflected in this inter partes review certificate under 35 U.S.C. 318(b).

INTER PARTES REVIEW CERTIFICATE
U.S. Patent 8,562,999 K2
Trial No. IPR2017-00378
Certificate Issued Oct. 25, 2021

AS A RESULT OF THE INTER PARTES REVIEW PROCEEDING, IT HAS BEEN DETERMINED THAT:

Claim 18 is found patentable.

Claims 1-6, 10, 11, 14, 17, 19 and 20 are cancelled.

\* \* \* \* \*